United States Patent
Cummings et al.

(10) Patent No.: US 7,369,252 B2
(45) Date of Patent: May 6, 2008

(54) PROCESS CONTROL MONITORS FOR INTERFEROMETRIC MODULATORS

(75) Inventors: William Cummings, Millbrae, CA (US); Brian Gally, Los Gatos, CA (US)

(73) Assignee: IDC, LLC, San Francisco, CA (US)

( * ) Notice: Subject to any disclaimer, the term of this patent is extended or adjusted under 35 U.S.C. 154(b) by 5 days.

(21) Appl. No.: 11/281,758

(22) Filed: Nov. 17, 2005

(65) Prior Publication Data

US 2006/0066864 A1 Mar. 30, 2006

Related U.S. Application Data

(62) Division of application No. 11/198,888, filed on Aug. 5, 2005.

(60) Provisional application No. 60/613,537, filed on Sep. 27, 2004.

(51) Int. Cl.
G01B 9/02 (2006.01)
G01B 11/02 (2006.01)
G02B 26/00 (2006.01)

(52) U.S. Cl. .................. 356/519; 356/503; 359/291

(58) Field of Classification Search ............. 356/503, 356/504, 519; 359/291
See application file for complete search history.

(56) References Cited

U.S. PATENT DOCUMENTS

| | | |
|---|---|---|
| 2,534,846 A | 12/1950 | Ambrose et al. |
| 3,439,973 A | 4/1969 | Paul et al. |
| 3,443,854 A | 5/1969 | Weiss |
| 3,653,741 A | 4/1972 | Marks |
| 3,656,836 A | 4/1972 | de Cremoux et al. |
| 3,813,265 A | 5/1974 | Marks |
| 3,899,295 A | 8/1975 | Halpem et al. |
| 3,955,880 A | 5/1976 | Lierke |
| 4,001,808 A | 1/1977 | Ebihara et al. |
| 4,099,854 A | 7/1978 | Decker et al. |
| 4,224,565 A | 9/1980 | Sosniak et al. |
| 4,228,437 A | 10/1980 | Shelton |
| 4,377,324 A | 3/1983 | Durand et al. |
| 4,389,096 A | 6/1983 | Hori et al. |

(Continued)

FOREIGN PATENT DOCUMENTS

CH 685887 A5 10/1995

(Continued)

OTHER PUBLICATIONS

Akasaka, "Three-Dimensional IC Trends," Proceedings of IEEE, vol. 74, No. 12, pp. 1703-1714 (Dec. 1986).

(Continued)

*Primary Examiner*—Patrick Connolly
(74) *Attorney, Agent, or Firm*—Knobbe Martens Olson & Bear LLP

(57) ABSTRACT

Process control monitors are disclosed that are produced using at least some of the same process steps used to manufacture a MEMS device. Analysis of the process control monitors can provide information regarding properties of the MEMS device and components or sub-components in the device. This information can be used to identify errors in processing or to optimize the MEMS device. In some embodiments, analysis of the process control monitors may utilize optical measurements.

12 Claims, 16 Drawing Sheets

U.S. PATENT DOCUMENTS

| | | | |
|---|---|---|---|
| 4,403,248 A | 9/1983 | te Velde | |
| 4,441,791 A | 4/1984 | Hornbeck | |
| 4,445,050 A | 4/1984 | Marks | |
| 4,482,213 A | 11/1984 | Piliavin et al. | |
| 4,500,171 A | 2/1985 | Penz et al. | |
| 4,519,676 A | 5/1985 | te Velde | |
| 4,531,126 A | 7/1985 | Sadones | |
| 4,566,935 A | 1/1986 | Hornbeck | |
| 4,571,603 A | 2/1986 | Hornbeck et al. | |
| 4,596,992 A | 6/1986 | Hornbeck | |
| 4,615,595 A | 10/1986 | Hornbeck | |
| 4,662,746 A | 5/1987 | Hornbeck | |
| 4,663,083 A | 5/1987 | Marks | |
| 4,681,403 A | 7/1987 | te Velde et al. | |
| 4,710,732 A | 12/1987 | Hornbeck | |
| 4,748,366 A | 5/1988 | Taylor | |
| 4,786,128 A | 11/1988 | Birnbach | |
| 4,790,635 A | 12/1988 | Apsley | |
| 4,856,863 A | 8/1989 | Sampsell et al. | |
| 4,897,360 A | 1/1990 | Guckel et al. | |
| 4,954,789 A | 9/1990 | Sampsell | |
| 4,956,619 A | 9/1990 | Hornbeck | |
| 4,982,184 A | 1/1991 | Kirkwood | |
| 5,018,256 A | 5/1991 | Hornbeck | |
| 5,022,745 A | 6/1991 | Zahowski et al. | |
| 5,028,939 A | 7/1991 | Hornbeck et al. | |
| 5,037,173 A | 8/1991 | Sampsell et al. | |
| 5,044,736 A | 9/1991 | Jaskie et al. | |
| 5,061,049 A | 10/1991 | Hornbeck | |
| 5,075,796 A | 12/1991 | Schildkraut et al. | |
| 5,078,479 A | 1/1992 | Vuilleumier | |
| 5,079,544 A | 1/1992 | DeMond et al. | |
| 5,083,857 A | 1/1992 | Hornbeck | |
| 5,096,279 A | 3/1992 | Hornbeck et al. | |
| 5,099,353 A | 3/1992 | Hornbeck | |
| 5,124,834 A | 6/1992 | Cusano et al. | |
| 5,142,405 A | 8/1992 | Hornbeck | |
| 5,153,771 A | 10/1992 | Link et al. | |
| 5,162,787 A | 11/1992 | Thompson et al. | |
| 5,168,406 A | 12/1992 | Nelson | |
| 5,170,156 A | 12/1992 | DeMond et al. | |
| 5,172,262 A | 12/1992 | Hornbeck | |
| 5,175,772 A | 12/1992 | Kahn et al. | |
| 5,179,274 A | 1/1993 | Sampsell | |
| 5,192,395 A | 3/1993 | Boysel et al. | |
| 5,192,946 A | 3/1993 | Thompson et al. | |
| 5,206,629 A | 4/1993 | DeMond et al. | |
| 5,214,419 A | 5/1993 | DeMond et al. | |
| 5,214,420 A | 5/1993 | Thompson et al. | |
| 5,216,537 A | 6/1993 | Hornbeck | |
| 5,226,099 A | 7/1993 | Mignardi et al. | |
| 5,231,532 A | 7/1993 | Magel et al. | |
| 5,233,385 A | 8/1993 | Sampsell | |
| 5,233,456 A | 8/1993 | Nelson | |
| 5,233,459 A | 8/1993 | Bozler et al. | |
| 5,254,980 A | 10/1993 | Hendrix et al. | |
| 5,272,473 A | 12/1993 | Thompson et al. | |
| 5,278,652 A | 1/1994 | Urbanus et al. | |
| 5,280,277 A | 1/1994 | Hornbeck | |
| 5,287,096 A | 2/1994 | Thompson et al. | |
| 5,296,950 A | 3/1994 | Lin et al. | |
| 5,305,640 A | 4/1994 | Boysel et al. | |
| 5,307,139 A | 4/1994 | Tyson, II et al. | |
| 5,311,360 A | 5/1994 | Bloom et al. | |
| 5,312,513 A | 5/1994 | Florence et al. | |
| 5,323,002 A | 6/1994 | Sampsell et al. | |
| 5,325,116 A | 6/1994 | Sampsell | |
| 5,327,286 A | 7/1994 | Sampsell et al. | |
| 5,331,454 A | 7/1994 | Hornbeck | |
| 5,339,116 A | 8/1994 | Urbanus et al. | |
| 5,365,283 A | 11/1994 | Doherty et al. | |
| 5,381,253 A | 1/1995 | Sharp et al. | |
| 5,401,983 A | 3/1995 | Jokerst et al. | |
| 5,411,769 A | 5/1995 | Hornbeck | |
| 5,444,566 A | 8/1995 | Gale et al. | |
| 5,446,479 A | 8/1995 | Thompson et al. | |
| 5,448,314 A | 9/1995 | Heimbuch et al. | |
| 5,452,024 A | 9/1995 | Sampsell | |
| 5,454,906 A | 10/1995 | Baker et al. | |
| 5,457,493 A | 10/1995 | Leddy et al. | |
| 5,457,566 A | 10/1995 | Sampsell et al. | |
| 5,459,409 A | 10/1995 | Henley | |
| 5,459,602 A | 10/1995 | Sampsell | |
| 5,459,610 A | 10/1995 | Bloom et al. | |
| 5,461,411 A | 10/1995 | Florence et al. | |
| 5,489,952 A | 2/1996 | Gove et al. | |
| 5,497,172 A | 3/1996 | Doherty et al. | |
| 5,497,197 A | 3/1996 | Gove et al. | |
| 5,499,062 A | 3/1996 | Urbanus | |
| 5,500,635 A | 3/1996 | Mott | |
| 5,500,761 A | 3/1996 | Goossen et al. | |
| 5,506,597 A | 4/1996 | Thompson et al. | |
| 5,515,076 A | 5/1996 | Thompson et al. | |
| 5,517,347 A | 5/1996 | Sampsell | |
| 5,523,803 A | 6/1996 | Urbanus et al. | |
| 5,526,051 A | 6/1996 | Gove et al. | |
| 5,526,172 A | 6/1996 | Kanack | |
| 5,526,688 A | 6/1996 | Boysel et al. | |
| 5,535,047 A | 7/1996 | Hornbeck | |
| 5,548,301 A | 8/1996 | Kornher et al. | |
| 5,551,293 A | 9/1996 | Boysel et al. | |
| 5,552,924 A | 9/1996 | Tregilgas | |
| 5,563,398 A | 10/1996 | Sampsell | |
| 5,567,334 A | 10/1996 | Baker et al. | |
| 5,570,135 A | 10/1996 | Gove et al. | |
| 5,579,149 A | 11/1996 | Moret et al. | |
| 5,581,272 A | 12/1996 | Conner et al. | |
| 5,583,688 A | 12/1996 | Hornbeck | |
| 5,589,852 A | 12/1996 | Thompson et al. | |
| 5,597,736 A | 1/1997 | Sampsell | |
| 5,600,383 A | 2/1997 | Hornbeck | |
| 5,602,671 A | 2/1997 | Hornbeck | |
| 5,606,441 A | 2/1997 | Florence et al. | |
| 5,608,468 A | 3/1997 | Gove et al. | |
| 5,610,438 A | 3/1997 | Wallace et al. | |
| 5,610,624 A | 3/1997 | Bhuva | |
| 5,610,625 A | 3/1997 | Sampsell | |
| 5,619,059 A | 4/1997 | Li et al. | |
| 5,619,365 A | 4/1997 | Rhoades et al. | |
| 5,619,366 A | 4/1997 | Rhoads et al. | |
| 5,636,052 A | 6/1997 | Arney et al. | |
| 5,646,768 A | 7/1997 | Kaeiyama | |
| 5,650,881 A | 7/1997 | Hornbeck | |
| 5,654,741 A | 8/1997 | Sampsell et al. | |
| 5,657,099 A | 8/1997 | Doherty et al. | |
| 5,659,374 A | 8/1997 | Gale, Jr. et al. | |
| 5,665,997 A | 9/1997 | Weaver et al. | |
| 5,703,710 A | 12/1997 | Brinkman et al. | |
| 5,710,656 A | 1/1998 | Goosen | |
| 5,729,245 A | 3/1998 | Gove et al. | |
| 5,739,945 A | 4/1998 | Tayebati | |
| 5,745,193 A | 4/1998 | Urbanus et al. | |
| 5,745,281 A | 4/1998 | Yi et al. | |
| 5,771,116 A | 6/1998 | Miller et al. | |
| 5,784,190 A | 7/1998 | Worley | |
| 5,784,212 A | 7/1998 | Hornbeck | |
| 5,818,095 A | 10/1998 | Sampsell | |
| 5,825,528 A | 10/1998 | Goossen | |
| 5,835,255 A | 11/1998 | Miles | |
| 5,842,088 A | 11/1998 | Thompson | |
| 5,912,758 A | 6/1999 | Knipe et al. | |
| 5,986,796 A | 11/1999 | Miles | |
| 6,028,690 A | 2/2000 | Carter et al. | |
| 6,038,056 A | 3/2000 | Florence et al. | |

| Patent/Pub No. | Date | Inventor |
|---|---|---|
| 6,040,937 A * | 3/2000 | Miles .................... 359/291 |
| 6,049,317 A | 4/2000 | Thompson et al. |
| 6,055,090 A * | 4/2000 | Miles .................... 359/291 |
| 6,061,075 A | 5/2000 | Nelson et al. |
| 6,088,474 A | 7/2000 | Dudasko et al. |
| 6,099,132 A | 8/2000 | Kaeriyama |
| 6,113,239 A | 9/2000 | Sampsell et al. |
| 6,147,790 A | 11/2000 | Meier et al. |
| 6,160,833 A | 12/2000 | Floyd et al. |
| 6,180,428 B1 | 1/2001 | Peeters et al. |
| 6,201,633 B1 | 3/2001 | Peeters et al. |
| 6,232,936 B1 | 5/2001 | Gove et al. |
| 6,282,010 B1 | 8/2001 | Sulzbach et al. |
| 6,285,207 B1 | 9/2001 | Listwan |
| 6,295,154 B1 | 9/2001 | Laor et al. |
| 6,323,982 B1 | 11/2001 | Hornbeck |
| 6,347,009 B1 | 2/2002 | Takeuchi |
| 6,407,560 B1 | 6/2002 | Walraven et al. |
| RE37,847 E | 9/2002 | Henley et al. |
| 6,447,126 B1 | 9/2002 | Hornbeck |
| 6,465,355 B1 | 10/2002 | Horsley |
| 6,466,358 B2 | 10/2002 | Tew |
| 6,473,274 B1 | 10/2002 | Maimone et al. |
| 6,480,177 B2 | 11/2002 | Doherty et al. |
| 6,496,122 B2 | 12/2002 | Sampsell |
| 6,545,335 B1 | 4/2003 | Chua et al. |
| 6,548,908 B2 | 4/2003 | Chua et al. |
| 6,549,338 B1 | 4/2003 | Wolverton et al. |
| 6,552,840 B2 | 4/2003 | Knipe |
| 6,567,715 B1 | 5/2003 | Sinclair et al. |
| 6,574,033 B1 | 6/2003 | Chui et al. |
| 6,589,625 B1 | 7/2003 | Kothari et al. |
| 6,600,201 B2 | 7/2003 | Hartwell et al. |
| 6,606,175 B1 | 8/2003 | Sampsell et al. |
| 6,625,047 B2 | 9/2003 | Coleman, Jr. |
| 6,630,786 B2 | 10/2003 | Cummings et al. |
| 6,632,698 B2 | 10/2003 | Ives |
| 6,643,069 B2 | 11/2003 | Dewald |
| 6,650,455 B2 | 11/2003 | Miles |
| 6,666,561 B1 | 12/2003 | Blakley |
| 6,674,090 B1 | 1/2004 | Chua et al. |
| 6,674,562 B1 | 1/2004 | Miles |
| 6,680,792 B2 | 1/2004 | Miles |
| 6,710,908 B2 | 3/2004 | Miles et al. |
| 6,741,377 B2 | 5/2004 | Miles |
| 6,741,384 B1 | 5/2004 | Martin et al. |
| 6,741,503 B1 | 5/2004 | Farris et al. |
| 6,747,785 B2 | 6/2004 | Chen et al. |
| 6,747,800 B1 | 6/2004 | Lin |
| 6,750,152 B1 | 6/2004 | Christenson et al. |
| 6,753,528 B1 | 6/2004 | Nikoonahad et al. |
| 6,775,174 B2 | 8/2004 | Huffman et al. |
| 6,778,155 B2 | 8/2004 | Doherty et al. |
| 6,791,758 B1 * | 9/2004 | Scobey .................... 359/584 |
| 6,794,119 B2 | 9/2004 | Miles |
| 6,811,267 B1 | 11/2004 | Allen et al. |
| 6,819,469 B1 | 11/2004 | Koba |
| 6,822,628 B2 | 11/2004 | Dunphy et al. |
| 6,824,739 B1 | 11/2004 | Arney et al. |
| 6,829,132 B2 | 12/2004 | Martin et al. |
| 6,853,129 B1 | 2/2005 | Cummings et al. |
| 6,855,610 B2 | 2/2005 | Tung et al. |
| 6,859,218 B1 | 2/2005 | Luman et al. |
| 6,861,277 B1 | 3/2005 | Monroe et al. |
| 6,862,022 B2 | 3/2005 | Slupe |
| 6,862,029 B1 | 3/2005 | D'Souza et al. |
| 6,867,896 B2 | 3/2005 | Miles |
| 6,870,581 B2 | 3/2005 | Li et al. |
| 6,870,654 B2 | 3/2005 | Lin et al. |
| 6,882,458 B2 | 4/2005 | Lin et al. |
| 6,882,461 B2 | 4/2005 | Tsai et al. |
| 6,894,786 B1 * | 5/2005 | Holbrook et al. .......... 356/454 |
| 6,912,022 B2 | 6/2005 | Lin et al. |
| 6,934,033 B2 * | 8/2005 | McDaniel et al. .......... 356/454 |
| 6,952,303 B2 | 10/2005 | Lin et al. |
| 6,958,847 B2 | 10/2005 | Lin |
| 7,061,681 B2 | 6/2006 | Anderson et al. |
| 7,123,216 B1 | 10/2006 | Miles |
| 7,259,865 B2 * | 8/2007 | Cummings et al. ......... 356/503 |
| 2001/0003487 A1 | 6/2001 | Miles |
| 2002/0015215 A1 | 2/2002 | Miles |
| 2002/0054424 A1 | 5/2002 | Miles |
| 2002/0075555 A1 | 6/2002 | Miles |
| 2002/0126364 A1 | 9/2002 | Miles |
| 2002/0157033 A1 | 10/2002 | Cox |
| 2003/0016361 A1 | 1/2003 | Mank |
| 2003/0043157 A1 | 3/2003 | Miles |
| 2003/0063081 A1 | 4/2003 | Kimura et al. |
| 2003/0072070 A1 | 4/2003 | Miles |
| 2003/0077881 A1 | 4/2003 | Gelmi et al. |
| 2003/0112231 A1 | 6/2003 | Kurumisawa |
| 2003/0202264 A1 | 10/2003 | Weber et al. |
| 2003/0202265 A1 | 10/2003 | Reboa et al. |
| 2003/0202266 A1 | 10/2003 | Ring et al. |
| 2004/0004610 A1 | 1/2004 | Iwami |
| 2004/0027636 A1 | 2/2004 | Miles |
| 2004/0051929 A1 | 3/2004 | Sampsell et al. |
| 2004/0057043 A1 | 3/2004 | Newman et al. |
| 2004/0058532 A1 | 3/2004 | Miles et al. |
| 2004/0070400 A1 | 4/2004 | van Spengen |
| 2004/0080807 A1 | 4/2004 | Chen et al. |
| 2004/0125281 A1 | 7/2004 | Lin et al. |
| 2004/0145049 A1 | 7/2004 | McKinnell et al. |
| 2004/0145811 A1 | 7/2004 | Lin et al. |
| 2004/0147056 A1 | 7/2004 | McKinnell et al. |
| 2004/0147198 A1 | 7/2004 | Lin et al. |
| 2004/0160143 A1 | 8/2004 | Shreeve et al. |
| 2004/0174583 A1 | 9/2004 | Chen et al. |
| 2004/0175577 A1 | 9/2004 | Lin et al. |
| 2004/0179281 A1 | 9/2004 | Reboa |
| 2004/0206953 A1 | 10/2004 | Morena et al. |
| 2004/0207897 A1 | 10/2004 | Lin |
| 2004/0209192 A1 | 10/2004 | Lin et al. |
| 2004/0209195 A1 | 10/2004 | Lin |
| 2004/0212026 A1 | 10/2004 | Van Brocklin et al. |
| 2004/0217378 A1 | 11/2004 | Martin et al. |
| 2004/0217919 A1 | 11/2004 | Pichi et al. |
| 2004/0218251 A1 | 11/2004 | Piehl et al. |
| 2004/0218334 A1 | 11/2004 | Martin et al. |
| 2004/0218341 A1 | 11/2004 | Martin et al. |
| 2004/0227493 A1 | 11/2004 | Van Brocklin et al. |
| 2004/0240032 A1 | 12/2004 | Miles |
| 2004/0240138 A1 | 12/2004 | Martin et al. |
| 2004/0245588 A1 | 12/2004 | Nikkel et al. |
| 2004/0262604 A1 | 12/2004 | Lee |
| 2004/0263944 A1 | 12/2004 | Miles et al. |
| 2005/0001828 A1 | 1/2005 | Martin et al. |
| 2005/0003667 A1 | 1/2005 | Lin et al. |
| 2005/0024557 A1 | 2/2005 | Lin |
| 2005/0035699 A1 | 2/2005 | Tsai |
| 2005/0036095 A1 | 2/2005 | Yeh et al. |
| 2005/0036192 A1 | 2/2005 | Lin et al. |
| 2005/0038950 A1 | 2/2005 | Adelmann |
| 2005/0042117 A1 | 2/2005 | Lin |
| 2005/0046922 A1 | 3/2005 | Lin et al. |
| 2005/0046948 A1 | 3/2005 | Lin |
| 2005/0057442 A1 | 3/2005 | Way |
| 2005/0068583 A1 | 3/2005 | Gutowski et al. |
| 2005/0068605 A1 | 3/2005 | Tsai |
| 2005/0068606 A1 | 3/2005 | Tsai |
| 2005/0069209 A1 | 3/2005 | Damera-Venkata et al. |
| 2005/0078348 A1 | 4/2005 | Lin |
| 2005/0168849 A1 | 8/2005 | Lin |
| 2005/0195462 A1 | 9/2005 | Lin |
| 2005/0202649 A1 | 9/2005 | Hung et al. |
| 2005/0249966 A1 | 11/2005 | Tung et al. |

| | | | |
|---|---|---|---|
| 2006/0066864 A1* | 3/2006 | Cummings et al. | 356/450 |
| 2006/0066871 A1* | 3/2006 | Cummings et al. | 356/503 |
| 2006/0066872 A1* | 3/2006 | Cummings et al. | 356/504 |
| 2006/0066876 A1* | 3/2006 | Kothari | 356/519 |
| 2006/0066935 A1 | 3/2006 | Cummings et al. | |
| 2006/0077381 A1* | 4/2006 | Cummings et al. | 356/237.6 |
| 2006/0077509 A1* | 4/2006 | Tung et al. | 359/260 |
| 2006/0077510 A1* | 4/2006 | Chui et al. | 359/260 |
| 2006/0176487 A1* | 8/2006 | Cummings et al. | 356/445 |
| 2006/0209384 A1* | 9/2006 | Chui et al. | 359/290 |
| 2007/0201038 A1* | 8/2007 | Cummings et al. | 356/519 |

FOREIGN PATENT DOCUMENTS

| | | |
|---|---|---|
| CH | 6855887 | 10/1995 |
| DE | 19525081 | 1/1997 |
| EP | 1065645 | 1/2001 |
| FR | 2516785 | 5/1983 |
| GB | 2030721 | 4/1980 |
| JP | 01259243 | 1/1990 |
| JP | 3002540 A | 1/1991 |
| JP | 11 337412 | 3/2000 |
| WO | WO 95/30924 | 11/1995 |
| WO | WO 97/17628 | 5/1997 |
| WO | WO 99/52006 A2 | 10/1999 |
| WO | WO 99/52006 A3 | 10/1999 |
| WO | WO 01/69310 A1 | 9/2001 |
| WO | WO 02/93116 A1 | 11/2002 |
| WO | WO 03/007049 A1 | 1/2003 |
| WO | WO 03/069413 A1 | 8/2003 |
| WO | WO 03/073151 A1 | 9/2003 |
| WO | WO 2004/006003 A1 | 1/2004 |
| WO | WO 2004/025239 A2 | 3/2004 |
| WO | WO 2004/026757 A2 | 4/2004 |
| WO | WO 2005/001410 A1 | 1/2005 |

OTHER PUBLICATIONS

Aratani et al., "Process and Design Considerations for Surface Micromachined Beams for a Tuneable Interferometer Array in Silicon," Proc. IEEE Microelectromechanical Workshop, Fort Lauderdate, FL, pp. 230-235 (Feb. 1993).

Aratani et al., "Surface Micromachined Tuneable Interferometer Array," Sensors and Actuatros, pp. 17-23 (1994).

Conner, "Hybrid Color Display Using Optical Interference Filter Array," SID Digest, pp. 577-580 (1993).

Durr et al., "Reliability Test And Failure Analysis Of Optical MEMS", Proceedings of the 9th International Symposium on the Physical and Failure Analysis of Integrated Circuits, pp. 201-206, (Jul. 8-12, 2002).

Goossen et al., "Possible Display Applications of the Silicon Mechanical Anti-Reflection Switch," Society for Information Display (1994).

Goossen et al., "Silicon Modulator Based on Mechanically-Active Anti-Reflection Layer with 1 Mbit/sec Capability for Fiber -in-the-Loop Applications," IEEE Photonics Technology Letters (Sep. 1994).

Gosch, "West Germany Grabs the Lead in X-Ray Lithography," Electronics, pp. 78-80 (Feb. 5, 1987).

Harpster Timothy J et al., "A Passive Humidity Monitoring System for In Situ Remote Wireless Testing of Micropackages," J. Microelectromech Syst. vol.11, No. 1, p. 61-67, (2002).

Howard et al., "Nanometer-Scale Fabrication Techniques," VLSI Electronics: Microstructure Science, vol. 5, pp. 145-153 and pp. 166-173 (1982).

Jerman et al., "A Miniature Fabry-Perot Interferometer with a Corrugated Silicon Diaphragm Support," IEEE Electron Devices Society (1988).

Johnson "Optical Scanners," Microwave Scanning Antennas, vol. 1, pp. 251-261 (1964).

Light over Matter. Circle No. 36 (Jun. 1993).

Miles, "a New Reflective FPD Technology Using Interferometric Modulation," Society for Information Display '97 Digest, Session 7.3.

Miles, "Inteferometric Modulation:MOEMS as an Enabling Technology for High-Performance Reflective Displays," Proceedings of the SPIE, vol.4985, p. 131-39. (2003).

Miles et al., "Digital Paper™ for Reflective Displays," J. of the Society for Information Display Soc. Inf. Display USA. vol. 11, No. 1, p. 209-215. (2003).

Newsbreaks, "Quantum-trench devices might operate at terahertz frequencies," Laser Focus World (May 1993).

Oliner et al., "Radiating Elements and Mutual Coupling," Microwave Scanning Antennas, vol. 2, p. 131-194 (1966).

Raley et al., "A Fabry-Perol Microinterferometer for Visible Wavelengths," IEEE Solid-State Sensor and Actuator Workshop, Hilton Head, SC (1992).

"Reflection/backscattering Probes," Ocean Optics, INC, Internet Article, p. 1-3. XP- 002358482. URL:http://web.archive.org/web/20040619022333/www.oceanoptics.com/products/reflectionprobes.asp> retreived on Jun. 19, 2004.

Roveti, "Choosing A Humidity Sensor: A Review Of Three Technologies", http://www.sencorsmag.com/articles/0701/54/main.shtml, (published prior to Sep. 17, 2004).

Skaggs et al, "Automatic Testing Of The Digital Micromirror Device", IEEE/LEOS 1996 Summer Topical Meetings, pp. 11-12, (Aug. 5-9, 1996).

Sperger et al., "High Performance Patterned all-Dielectric Interference Colour Filter for Display Applications," SID Digest, pp. 81-83 (1994).

Stone, "Radiation and Optics, An Introduction to the Classical Theory," McGraw-Hill, pp. 340-343 (1963).

Tabata et al., "In Situ Observation and Analysis of Wet Etching Process for Micro electro-mechanical systems," Proc. Of the Workshop on Micro Electro Mechanical Systems. vol. Workshop 4. p. 99-102, (1991).

Walker, et al., "Electron-beam-tunable Interference Filter Spatial Light Modulator," Optics Letters vol. 13, No. 5, pp. 345-347 (May 1988).

Waelti M. et al., "Package Quality Testing Using Integrated Pressure Sensor," Proc. Of the SPIE, vol. 3582, p. 981-986, 1998).

Winton, John M., "A novel way to capture solar energy," Chemical Week, pp. 17-18 (May 15, 1985).

Wu, "Design of a Reflective Color LCD Using Optical Interference Reflectors," Asia Display'95, pp. 929-931 (Oct. 16, 1995).

International Search Report PCT Application No. PCT/US2005/033221, Dated Feb. 6, 2006.

Drieenhuizen, et al., "Comparison of Techniques for measuring Both Compressive and Tensile Stress in Thin Films," *Sensors and Actuators*, vol. 37-38, pp. 759-765. (1993).

Guckel et al., "Fine-Grained Polysilicon Films with Built-In Tensile Strain," *IEEE Transactions on Electron Devices*, vol. 35, No. 6, pp. 801-802, (1988).

"High-reflectivity Specular Reflectance standard," [Online] XP002374849, (URL:http://web/archive.org/web/20040220134330/www.oceanoptics.com/products/stan.ss1.asp> (retrieved on Feb. 20, 2004).

Lin et al., "A Micro Strain Gauge with Mechanical Amplifier," *J. of Microelectromechanical Systems*, vol. 6, No. 4, (1997).

"Low-reflectivity Specular Reflectance Standard," Internet Article, XP002374848 >URL:http://web.archive.org/web/20040220134257/www.oceanoptics.com/Productsstan.ss1.asp> (retrieved on Feb. 20, 2004).

Pruessner et al., "Mechanical Property Measurement of InP-based MEMS for optical communications," *Sensors and Actuators*, vol. 105, pp. 190-200, (2003).

"S2000 Miniature Fiber Optic Spectrometer", Internet Article, XP002358483, pp. 1-2, <URL:http://web.archive.org/web/20040617035842/www.oceanoptics.com/products/s2000.asp> (Retrieved Jun. 17, 2004.

Singh et al., "Strain Studies in LPCVD Polysilicon for Surface Micromachined Devices," *Sensors and Actuators*, vol. 77, pp. 133-138, (1999).

Srikar et al., "A Critical Review of Microscale Mechanical Testing Methods Used in the Design of Microelectromechanical Systems," *Society for Experimental mechanics,* vol. 43, No. 3, (2003).

Zhang, et al., "Measurements of Residual Stresses in Thin Films Using Micro-Rotating-Structures." *Thin Solid Films,* vol. 335, pp. 97-105, (1998).

Dokmeci, et al. *A High-Sensitivity Polyimide Capacitive Relative Humidity Sensor for Monitoring Anodically Bonded Hermetic Micropackages* Journal of Microelectromechanical Systems, vol. 10, No. 2, Jun. 2001, 197-204.

Jin, et al. "MEMS Vaccuum Packaging Technology and Applications" Electronics Packaging Technology, 2003, 5th Conference, Dec. 10-12, 2003, Piscataway, NJ, pp. 301-306.

Tominette, et al, Moisture and Impurities Detection and removal in Packaged MEMS, proceeding of SPIE vol. 4558, (2001), pp. 215-225.

IPRP for PCT/US05/033221 filed Sep. 16, 2005.

Office Action mailed Dec. 19, 2006 in U.S. Appl. No. 11/281,136.

* cited by examiner

PROCESS CONTROL MONITORS FOR INTERFEROMETRIC MODULATORS

CROSS-REFERENCE TO RELATED APPLICATIONS

This application is a divisional of U.S. application Ser. No. 11/198,888, filed Aug. 5, 2005, which claims priority to U.S. Provisional Application No. 60/613,537, filed on Sep. 27, 2004, both of which are incorporated herein by reference in their entirety. This application is also related to co-pending application Ser. No. 11/281,763, entitled "Process Control Monitors for Interferometric Modulators," filed Nov. 17, 2005, application Ser. No. 11/281,136, entitled "Process Control Monitors for Interferometric Modulators," filed Nov. 17, 2005, and application Ser. No. 11/281,176, entitled "Process Control Monitors for Interferometric Modulators," filed Nov. 17, 2005, all of which are incorporated herein by reference in their entirety.

BACKGROUND OF THE INVENTION

1. Field of the Invention

The field of the invention relates to microelectromechanical systems (MEMS).

2. Description of the Related Art

Microelectromechanical systems (MEMS) include micro mechanical elements, actuators, and electronics. Micromechanical elements may be created using deposition, etching, and or other micromachining processes that etch away parts of substrates and/or deposited material layers or that add layers to form electrical and electromechanical devices. One type of MEMS device is called an interferometric modulator. As used herein, the term interferometric modulator or interferometric light modulator refers to a device that selectively absorbs and/or reflects light using the principles of optical interference. In certain embodiments, an interferometric modulator may comprise a pair of conductive plates, one or both of which may be transparent and/or reflective in whole or part and capable of relative motion upon application of an appropriate electrical signal. In a particular embodiment, one plate may comprise a stationary layer deposited on a substrate and the other plate may comprise a metallic membrane separated from the stationary layer by an air gap. As described herein in more detail, the position of one plate in relation to another can change the optical interference of light incident on the interferometric modulator. Such devices have a wide range of applications, and it would be beneficial in the art to utilize and/or modify the characteristics of these types of devices so that their features can be exploited in improving existing products and creating new products that have not yet been developed.

Errors can occur during the manufacturing of MEMS devices. Detecting the errors and the source of the errors can present a problem in the quality control and optimization of MEMS devices. Accordingly, there is a need for structures and methods for monitoring manufacturing processes and their results.

SUMMARY OF THE INVENTION

One embodiment disclosed herein includes a method of obtaining information regarding manufacturing processes used to manufacture a micro-electro-mechanical system (MEMS), the method including forming at least one MEMS structure on a first side of a substrate through a series of deposition and patterning steps, simultaneously forming at least one process control monitor on the first side of the substrate utilizing the series of deposition and patterning steps, wherein the process control monitor has at least one structural difference from the MEMS structure, and detecting light reflected from the process control monitor from a second side of the substrate opposite the first side, whereby the detected light provides a characteristic of at least one material deposited or removed during the deposition and patterning steps.

Another embodiment disclosed herein includes a method of monitoring interferometric modulator manufacturing processes, wherein the manufacturing process comprises a series of deposition and patterning steps, the method including forming a process control monitor using the series of deposition and patterning steps, wherein the process control monitor has at least one structural difference from interferometric modulators formed by the manufacturing process and detecting optical reflectance from the process control monitor.

Another embodiment disclosed herein includes a process control monitor for use in monitoring interferometric modulator manufacturing processes, wherein the interferometric modulators are adapted for use in a display, the process control monitor manufactured by a process comprising at least one step in common with steps used to manufacture the interferometric modulators adapted for use in the display.

Another embodiment disclosed herein includes a wafer, comprising one or more interferometric modulators adapted for use in a display and one or more process control monitors adapted to reflect incident light and thereby provide information regarding processes used to manufacture the one or more interferometric modulators.

Another embodiment disclosed herein includes a wafer, comprising a plurality of first means for reflecting light for use in a display and second means for monitoring processes used to manufacture the first means.

Another embodiment disclosed herein includes a display, comprising a first wafer that comprises a plurality of interferometric modulators, wherein the first wafer is produced by a process comprising forming the plurality of interferometric modulators and at least one process control monitor on a second wafer and cutting the second wafer to remove the process control monitor and thereby produce the first wafer.

Another embodiment disclosed herein includes a method of identifying an array of interferometric modulators as suitable for use in a display, wherein the interferometric modulators are manufactured by a process comprising a series of deposition and patterning steps, the method including forming at least one process control monitor using at least some of the series of deposition and patterning steps and detecting at least one characteristic of the process control monitor.

Another embodiment disclosed herein includes a method of monitoring the extent of etching of a first material positioned between and adjacent to two layers of other material during manufacturing of a micro-electro-mechanical system (MEMS), the method including manufacturing a process control monitor that comprises the two layers of other material and the first material disposed between and adjacent to the two layers, wherein one of the two layers comprises a hole, exposing the hole to an etchant, and optically detecting a distance from the center of the hole to where the etchant has etched away the first material, whereby the distance is indicative of the extent of etching of the first material.

Another embodiment disclosed herein includes a wafer, comprising a plurality of structures comprising a sacrificial layer and at least one layer above and adjacent to the sacrificial layer, wherein the structures become interferometric modulators upon removal of the sacrificial layer, wherein the at least one layer above and adjacent to the sacrificial layer comprises a plurality of holes through which an etchant can reach the sacrificial layer and a process control monitor also comprising the sacrificial layer and the at least one layer above and adjacent to the sacrificial layer, wherein the at least one layer above and adjacent to the sacrificial layer in the process control monitor comprises multiple holes, wherein the distance between the holes in the process control monitor is greater than the distance between the plurality of holes in the plurality of structures.

Another embodiment disclosed herein includes a wafer, comprising a plurality of structures comprising a sacrificial layer and at least one layer above and adjacent to the sacrificial layer, wherein the structures become interferometric modulators upon removal of the sacrificial layer, wherein the at least one layer above and adjacent to the sacrificial layer comprises a plurality of holes through which an etchant can reach the sacrificial layer and a process control monitor also comprising the sacrificial layer and the at least one layer above and adjacent to the sacrificial layer, wherein the at least one layer above and adjacent to the sacrificial layer in the process control monitor comprises a single hole.

Another embodiment disclosed herein includes a method of manufacturing a wafer having a micro-electro-mechanical system (MEMS) and a process control monitor structure, the method including forming a plurality of structures, wherein forming the plurality of structures includes one or more material deposition and removal steps, wherein the structures comprise a sacrificial layer and at least one layer above and adjacent to the sacrificial layer, wherein the at least one layer above and adjacent to the sacrificial layer comprises a plurality of holes through which an etchant can reach the sacrificial layer, simultaneously forming a process control monitor, wherein forming the process control monitor includes the one or more material deposition and removal steps, wherein the process control monitor also comprises the sacrificial layer and the at least one layer above and adjacent to the sacrificial layer, wherein the at least one layer above and adjacent to the sacrificial layer in the process control monitor comprises multiple holes, wherein the distance between the holes in the process control monitor is greater than the distance between the plurality of holes in the plurality of structures, and exposing the plurality of structures and the process control monitor to an etchant.

Another embodiment disclosed herein includes a wafer, comprising: a micro-electro-mechanical structure (MEMS) and means for measuring extent of etching of a material removed during manufacturing of the MEMS.

Another embodiment disclosed herein includes a process control monitor produced by process including depositing at least three layers of material on top of each other and forming a hole in the top layer of material.

Another embodiment disclosed herein includes a method for determining the effect of an interferometric modulator manufacturing process on color reflected from interferometric modulators manufactured by the process, the method including manufacturing a plurality of interferometric modulators comprising posts that support a first mechanical membrane, manufacturing a process control monitor etalon comprising posts that support a second mechanical membrane, wherein the posts in the process control monitor are present in higher density than the posts in the plurality of interferometric modulators, and detecting light reflected from the process control monitor etalon, whereby the detected light provides an indication of the depth of an interferometric cavity in the plurality of interferometric modulators.

Another embodiment disclosed herein includes a process control monitor for monitoring the effect of a process for manufacturing interferometric modulators on color reflected by those interferometric modulators, comprising a test etalon that comprises a higher density of posts supporting a mechanical membrane in the test etalon than in interferometric modulators produced by the process.

Another embodiment disclosed herein includes a wafer, comprising a plurality of interferometric modulators adapted for use in a display and a process control monitor that comprises an etalon having a higher density of posts supporting a mechanical membrane than in the plurality of interferometric modulators.

Another embodiment disclosed herein includes a process control monitor, omc;idomg an etalon having a conductive partial mirror and a conductive mechanical membrane comprising a mirror, wherein the mechanical membrane is separated from the partial mirror by a plurality of posts, wherein the density of posts is high enough such that the mechanical membrane cannot collapse toward the partial mirror when a voltage is applied between the partial mirror and the mechanical membrane.

Another embodiment disclosed herein includes a method of manufacturing a combined micro-electro-mechanical system (MEMS) and process control monitor structure, the method including forming a MEMS structure, wherein forming the MEMS structure includes one or more material deposition and patterning steps, wherein the MEMS structure comprises a first mechanical membrane supported by a first plurality of posts and simultaneously forming a process control monitor, wherein forming the process control monitor includes the one or more material deposition and patterning steps, the process control monitor comprising a second mechanical membrane supported by a second plurality of posts, wherein the second plurality of posts are present in a higher density than the first plurality of posts.

Another embodiment disclosed herein includes a wafer, comprising a plurality of first means for reflecting light for use in a display and second means for stably reflecting light having substantially the same color as reflected from at least one of the second means.

Another embodiment disclosed herein includes a process control monitor produced by a process that includes forming a partial mirror, forming a mechanical membrane, and forming a plurality of posts supporting the mechanical membrane and separating the mechanical membrane from the partial mirror, wherein the density of posts is high enough such that the mechanical membrane cannot collapse toward the partial mirror when a voltage is applied between the partial mirror and the mechanical membrane.

Another embodiment disclosed herein includes a method of monitoring deposition of material deposited during manufacturing of a micro-electro-mechanical system (MEMS), the method including forming a process control monitor that consists of at least three layers of material deposited during the manufacturing, wherein the at least three layers of material is less than the number of layers deposited during manufacturing of the MEMS, wherein the at least three layers of material form an etalon and detecting light reflected from the etalon, whereby information regarding properties of the at least three layers is obtained.

Another embodiment disclosed herein includes a wafer, comprising a plurality of interferometric modulators adapted for use in a display and a non-modulating interferometer.

Another embodiment disclosed herein includes a method of monitoring deposition of material deposited during manufacturing of a micro-electro-mechanical system (MEMS), the method including forming a process control monitor comprising one or more layers of material deposited during the manufacturing, wherein the number of layers of material in the process control monitor is less than the number of layers deposited during manufacturing of the MEMS and detecting the reflectance of the process control monitor, whereby the reflectance provides information regarding properties of the layers in the process control monitor.

Another embodiment disclosed herein includes a wafer, comprising a plurality of interferometric modulators adapted for use in a display, the interferometric modulators comprising a plurality of material layers and a process control monitor comprising one or more of the material layers, wherein the process control monitor comprises less than all of the plurality of material layers.

Another embodiment disclosed herein includes a method of manufacturing a combined micro-electro-mechanical system (MEMS) and process control monitor structure, the method including forming a MEMS structure, wherein forming the MEMS structure includes one or more material deposition and patterning steps and simultaneously forming a process control monitor, wherein forming the process control monitor includes the one or more material deposition and patterning steps, wherein the process control monitor comprises less than all components present in the MEMS structure.

Another embodiment disclosed herein includes a wafer produced by a process that includes depositing and patterning a series of material layers on a substrate to form a MEMS structure and simultaneously depositing and patterning a series of material layers on the substrate to form a process control monitor, wherein the process control monitor comprises less than all components present in the MEMS structure.

Another embodiment disclosed herein includes a method of measuring thicknesses of layers deposited during manufacture of a micro-electro-mechanical system (MEMS), the method including forming a structure that comprises two or more layers successively deposited on top of each other, wherein the layers are formed using a process that is used for forming those layers during manufacture of the MEMS, wherein the layers are patterned such that at least two steps are formed in a profile of the structure and measuring the height of the steps by sweeping a profilometer across the structure.

Another embodiment disclosed herein includes a process control monitor for measuring the thicknesses of a plurality of layers deposited during manufacturing of an interferometric modulator, comprising the layers stacked on top of each other so as to form at least two steps in a profile of the process control monitor.

Another embodiment disclosed herein includes a wafer, comprising a plurality of interferometric modulators adapted for use in a display, the interferometric modulators comprising a plurality of material layers and a process control monitor comprising the plurality of material layers stacked on top of each other so as to form at least two steps in a profile of the process control monitor.

Another embodiment disclosed herein includes a method of manufacturing a combined micro-electro-mechanical system (MEMS) and process control monitor structure, the method including forming a MEMS structure, wherein forming the MEMS structure includes one or more material deposition and patterning steps, wherein the MEMS structure comprises a plurality of layers and simultaneously forming a process control monitor, wherein forming the process control monitor includes the one or more material deposition and patterning steps, wherein the process control monitor comprises the plurality of layers so as to form at least two steps in a profile of the process control monitor.

Another embodiment disclosed herein includes a wafer, comprising a plurality of first means for reflecting light for use in a display and second means for measuring thickness of at least one material deposited during manufacture of the first means.

Another embodiment disclosed herein includes a wafer produced by a process comprising depositing and patterning a series of material layers on a substrate to form a MEMS structure and simultaneously depositing and patterning the series of material layers on the substrate to form a process control monitor, wherein layers of material remaining in the process control monitor after the patterning form at least two steps in a profile of the process control monitor.

Another embodiment disclosed herein includes a method of testing a process used to manufacture a polychromatic interferometric modulator display, wherein different color interferometric modulators in the display are manufactured by forming different depth gaps between a partial reflector and a reflective mechanical membrane, wherein the depths of the gaps are determined by deposition of one or more sacrificial layers, wherein the depth of at least one gap is determined by deposition of a plurality of sacrificial layers, the method including forming a process control monitor that comprises the one or more sacrificial layers, wherein at least one region of the process control monitor comprises the plurality of sacrificial layers deposited on top of each other, measuring a profile of the process control monitor, and determining a cumulative thickness of the plurality of sacrificial layers from the profile.

Another embodiment disclosed herein includes a process control monitor for use in testing a process used to manufacture a polychromatic interferometric modulator display, wherein different color interferometric modulators in the display are manufactured by forming different depth gaps between a partial reflector and a reflective mechanical membrane, wherein the depths of the gaps are determined by deposition of one or more sacrificial layers, wherein the depth of at least one gap is determined by deposition of a plurality of sacrificial layers, the process control monitor comprising a plurality of material layers on top of each other, wherein one region of the process control monitor includes a single sacrificial layer, a second region of the process control monitor includes two sacrificial layers on top of each other, and a third region of the process control monitor includes three sacrificial layers on top of each other.

DETAILED DESCRIPTION OF CERTAIN EMBODIMENTS

The following detailed description is directed to certain specific embodiments of the invention. However, the invention can be embodied in a multitude of different ways. In this description, reference is made to the drawings wherein like parts are designated with like numerals throughout. As will be apparent from the following description, the embodiments may be implemented in any device that is configured to display an image, whether in motion (e.g., video) or stationary (e.g., still image), and whether textual or pictorial. More particularly, it is contemplated that the embodiments may be implemented in or associated with a variety of electronic devices such as, but not limited to, mobile telephones, wireless devices, personal data assistants (PDAs), hand-held or portable computers, GPS receivers/navigators, cameras, MP3 players, camcorders, game consoles, wrist watches, clocks, calculators, television monitors, flat panel displays, computer monitors, auto displays (e.g., odometer display, etc.), cockpit controls and/or displays, display of camera views (e.g., display of a rear view camera in a vehicle), electronic photographs, electronic billboards or signs, projectors, architectural structures, packaging, and aesthetic structures (e.g., display of images on a piece of jewelry). MEMS devices of similar structure to those described herein can also be used in non-display applications such as in electronic switching devices.

Manufacturing of MEMS devices typically involve the formation of several layers of material having structures and thicknesses formed by using a series of material deposition, patterning, and etching steps. It can be difficult to diagnose from the final MEMS device any errors that occurred during the processing of given layers in the device. Furthermore, it can be difficult to determine from the final device which specific parameters, such as film thicknesses, should be adjusted in order to optimize the device for its intended use. Accordingly, there is a need for structures and methods that can be used to monitor the result of specific processing steps. Therefore, in various embodiments, process control monitors are provided that are constructed using at least some of the same processes used to manufacture MEMS devices. Analysis of the process control monitors provide information regarding individual components or sub-sets of components that make up the MEMS device.

Figure 1:
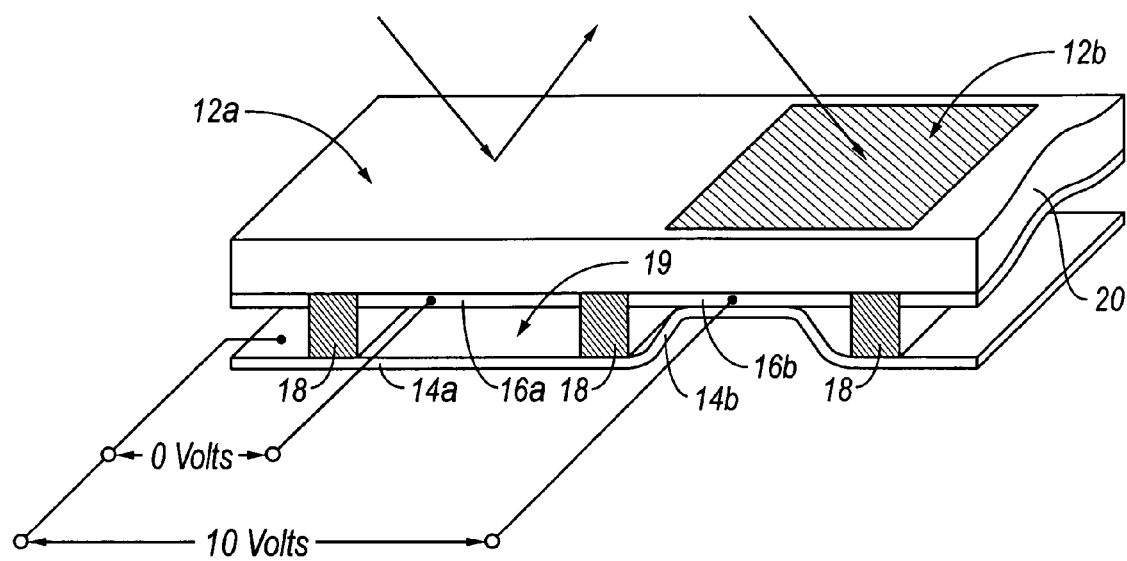
FIG. 1 is an isometric view depicting a portion of one embodiment of an interferometric modulator display in which a movable reflective layer of a first interferometric modulator is in a relaxed position and a movable reflective layer of a second interferometric modulator is in an actuated position.

One interferometric modulator display embodiment comprising an interferometric MEMS display element is illustrated in FIG. 1. In these devices, the pixels are in either a bright or dark state. In the bright ("on" or "open") state, the display element reflects a large portion of incident visible light to a user. When in the dark ("off" or "closed") state, the display element reflects little incident visible light to the user. Depending on the embodiment, the light reflectance properties of the "on" and "off" states may be reversed. MEMS pixels can be configured to reflect predominantly at selected colors, allowing for a color display in addition to black and white.

FIG. 1 is an isometric view depicting two adjacent pixels in a series of pixels of a visual display, wherein each pixel comprises a MEMS interferometric modulator. In some embodiments, an interferometric modulator display comprises a row/column array of these interferometric modulators. Each interferometric modulator includes a pair of reflective layers positioned at a variable and controllable distance from each other to form a resonant optical cavity with at least one variable dimension. In one embodiment, one of the reflective layers may be moved between two positions. In the first position, referred to herein as the relaxed position, the movable reflective layer is positioned at a relatively large distance from a fixed partially reflective layer. In the second position, referred to herein as the actuated position, the movable reflective layer is positioned more closely adjacent to the partially reflective layer. Incident light that reflects from the two layers interferes constructively or destructively depending on the position of the movable reflective layer, producing either an overall reflective or non-reflective state for each pixel.

The depicted portion of the pixel array in FIG. 1 includes two adjacent interferometric modulators 12a and 12b. In the interferometric modulator 12a on the left, a movable reflective layer 14a is illustrated in a relaxed position at a predetermined distance from an optical stack 16a, which includes a partially reflective layer. In the interferometric modulator 12b on the right, the movable reflective layer 14b is illustrated in an actuated position adjacent to the optical stack 16b.

The optical stacks 16a and 16b (collectively referred to as optical stack 16), as referenced herein, typically comprise of several fused layers, which can include an electrode layer, such as indium tin oxide (ITO), a partially reflective layer, such as chromium, and a transparent dielectric. The optical stack 16 is thus electrically conductive, partially transparent and partially reflective, and may be fabricated, for example, by depositing one or more of the above layers onto a transparent substrate 20. In some embodiments, the layers are patterned into parallel strips, and may form row electrodes in a display device as described further below. The movable reflective layers 14a, 14b may be formed as a series of parallel strips of a deposited metal layer or layers (orthogonal to the row electrodes of 16a, 16b) deposited on top of posts 18 and an intervening sacrificial material deposited between the posts 18. When the sacrificial material is etched away, the movable reflective layers 14a, 14b are separated from the optical stacks 16a, 16b by a defined gap 19. A highly conductive and reflective material such as aluminum may be used for the reflective layers 14, and these strips may form column electrodes in a display device.

With no applied voltage, the cavity 19 remains between the movable reflective layer 14a and optical stack 16a, with the movable reflective layer 14a in a mechanically relaxed state, as illustrated by the pixel 12a in FIG. 1. However, when a potential difference is applied to a selected row and column, the capacitor formed at the intersection of the row and column electrodes at the corresponding pixel becomes charged, and electrostatic forces pull the electrodes together. If the voltage is high enough, the movable reflective layer 14 is deformed and is forced against the optical stack 16. A dielectric layer (not illustrated in this Figure) within the optical stack 16 may prevent shorting and control the separation distance between layers 14 and 16, as illustrated by pixel 12b on the right in FIG. 1. The behavior is the same regardless of the polarity of the applied potential difference. In this way, row/column actuation that can control the reflective vs. non-reflective pixel states is analogous in many ways to that used in conventional LCD and other display technologies.

FIGS. 2 through 5B illustrate one exemplary process and system for using an array of interferometric modulators in a display application.

Figure 2:
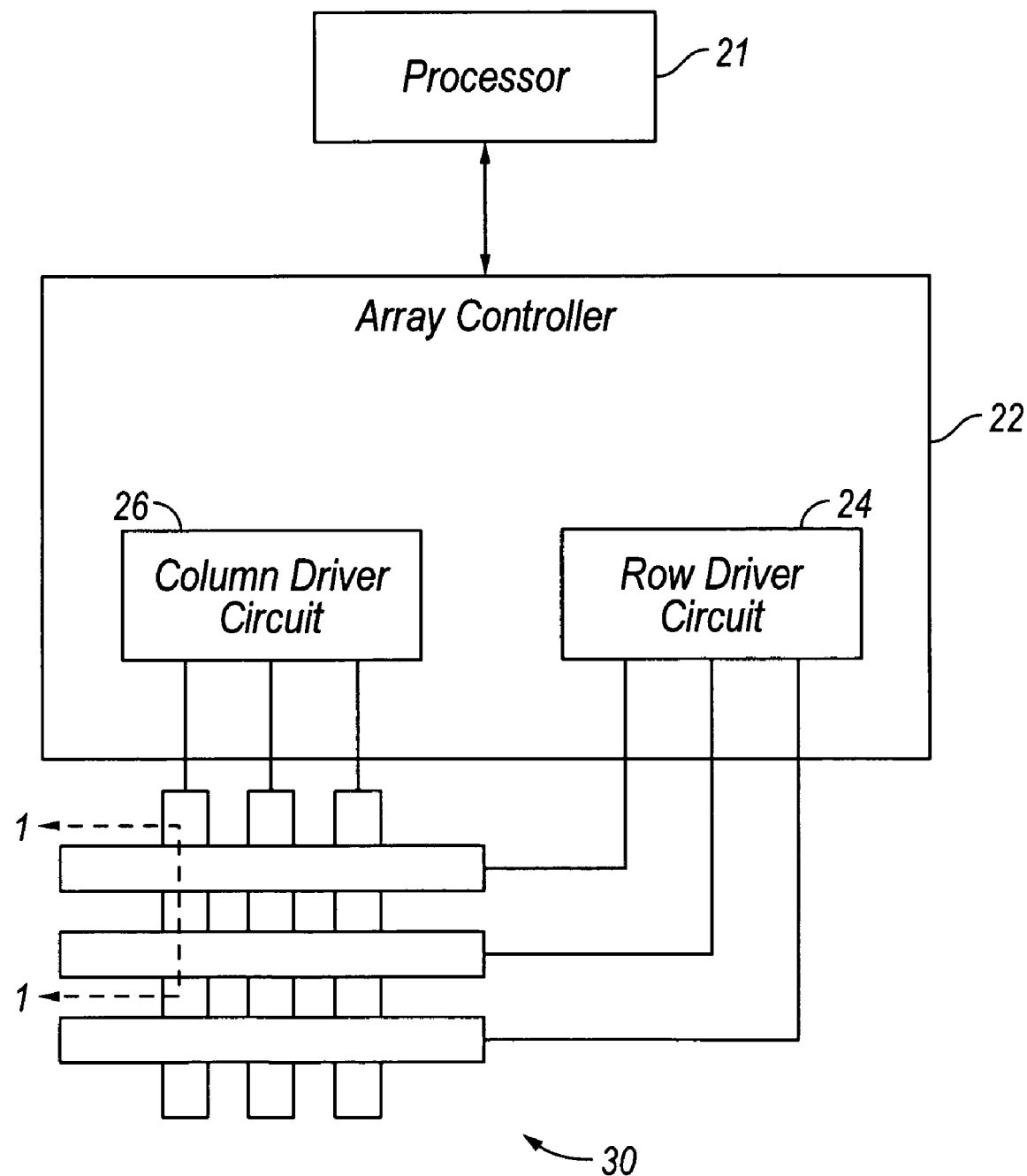
FIG. 2 is a system block diagram illustrating one embodiment of an electronic device incorporating a 3×3 interferometric modulator display.

FIG. 2 is a system block diagram illustrating one embodiment of an electronic device that may incorporate aspects of the invention. In the exemplary embodiment, the electronic device includes a processor 21 which may be any general purpose single- or multi-chip microprocessor such as an ARM, Pentium®, Pentium II®, Pentium III®, Pentium IV®, Pentium® Pro, an 8051, a MIPS®, a Power PC®, an ALPHA®, or any special purpose microprocessor such as a digital signal processor, microcontroller, or a programmable gate array. As is conventional in the art, the processor 21 may be configured to execute one or more software modules. In addition to executing an operating system, the processor may be configured to execute one or more software applications, including a web browser, a telephone application, an email program, or any other software application.

In one embodiment, the processor 21 is also configured to communicate with an array driver 22. In one embodiment, the array driver 22 includes a row driver circuit 24 and a column driver circuit 26 that provide signals to a panel or display array (display) 30. The cross section of the array illustrated in FIG. 1 is shown by the lines 1-1 in FIG. 2. For MEMS interferometric modulators, the row/column actuation protocol may take advantage of a hysteresis property of these devices illustrated in FIG. 3. It may require, for example, a 10 volt potential difference to cause a movable layer to deform from the relaxed state to the actuated state. However, when the voltage is reduced from that value, the movable layer maintains its state as the voltage drops back below 10 volts. In the exemplary embodiment of FIG. 3, the movable layer does not relax completely until the voltage drops below 2 volts. There is thus a range of voltage, about 3 to 7 V in the example illustrated in FIG. 3, where there exists a window of applied voltage within which the device is stable in either the relaxed or actuated state. This is referred to herein as the "hysteresis window" or "stability window." For a display array having the hysteresis characteristics of FIG. 3, the row/column actuation protocol can be designed such that during row strobing, pixels in the strobed row that are to be actuated are exposed to a voltage difference of about 10 volts, and pixels that are to be relaxed are exposed to a voltage difference of close to zero volts. After the strobe, the pixels are exposed to a steady state voltage difference of about 5 volts such that they remain in whatever state the row strobe put them in. After being written, each pixel sees a potential difference within the "stability window" of 3-7 volts in this example. This feature makes the pixel design illustrated in FIG. 1 stable under the same applied voltage conditions in either an actuated or relaxed pre-existing state. Since each pixel of the interferometric modulator, whether in the actuated or relaxed state, is essentially a capacitor formed by the fixed and moving reflective layers, this stable state can be held at a voltage within the hysteresis window with almost no power dissipation. Essentially no current flows into the pixel if the applied potential is fixed.

In typical applications, a display frame may be created by asserting the set of column electrodes in accordance with the desired set of actuated pixels in the first row. A row pulse is then applied to the row 1 electrode, actuating the pixels corresponding to the asserted column lines. The asserted set of column electrodes is then changed to correspond to the desired set of actuated pixels in the second row. A pulse is then applied to the row 2 electrode, actuating the appropriate pixels in row 2 in accordance with the asserted column electrodes. The row 1 pixels are unaffected by the row 2 pulse, and remain in the state they were set to during the row 1 pulse. This may be repeated for the entire series of rows in a sequential fashion to produce the frame. Generally, the frames are refreshed and/or updated with new display data by continually repeating this process at some desired number of frames per second. A wide variety of protocols for driving row and column electrodes of pixel arrays to produce display frames are also well known and may be used in conjunction with the present invention.

Figures 3, 4:
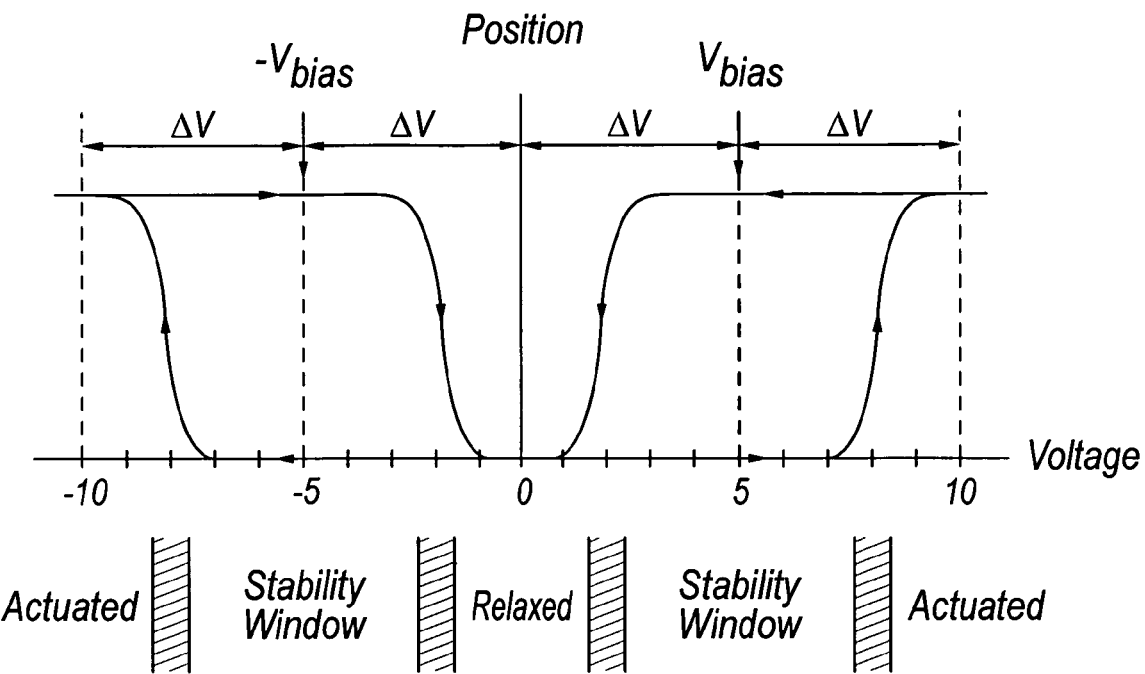
FIG. 3 is a diagram of movable mirror position versus applied voltage for one exemplary embodiment of an interferometric modulator of FIG. 1.
FIG. 4 is an illustration of a set of row and column voltages that may be used to drive an interferometric modulator display.
Figure 5A:
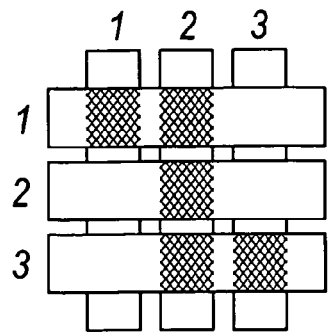
FIG. 5A illustrates one exemplary frame of display data in the 3×3 interferometric modulator display of FIG. 2.
Figure 5B:
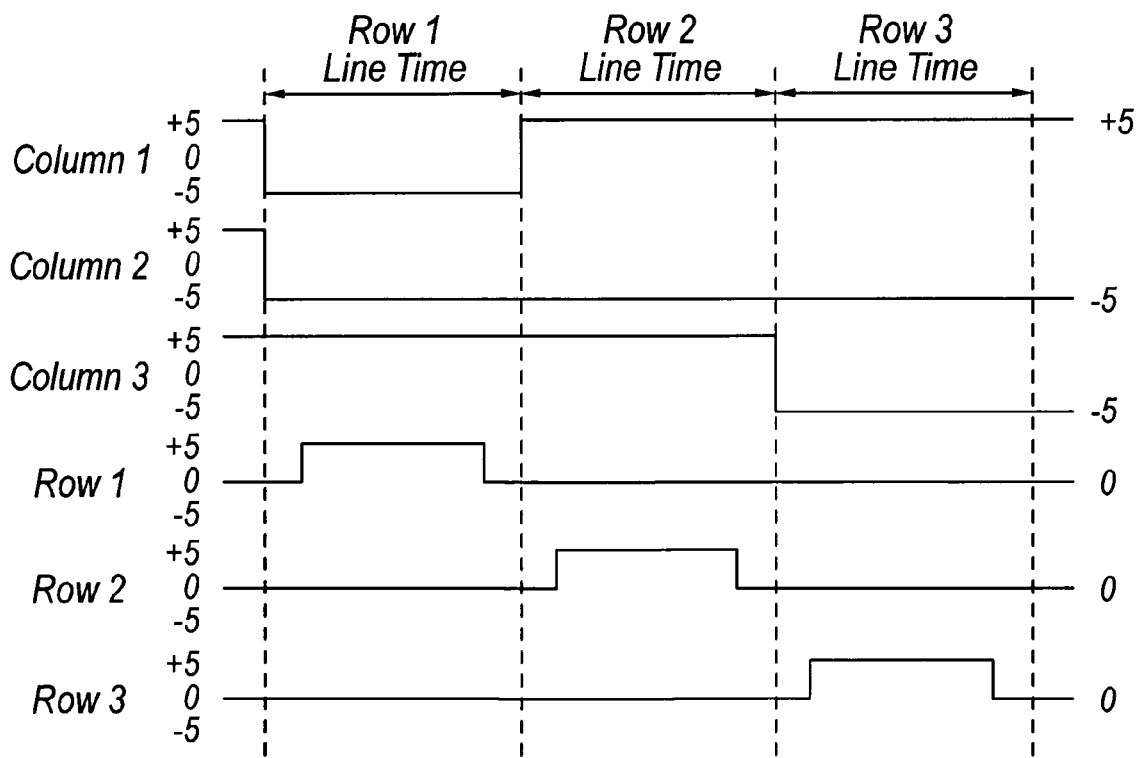
FIG. 5B illustrates one exemplary timing diagram for row and column signals that may be used to write the frame of FIG. 5A.

FIGS. 4, 5A, and 5B illustrate one possible actuation protocol for creating a display frame on the 3×3 array of FIG. 2. FIG. 4 illustrates a possible set of column and row voltage levels that may be used for pixels exhibiting the hysteresis curves of FIG. 3. In the FIG. 4 embodiment, actuating a pixel involves setting the appropriate column to $-V_{bias}$, and the appropriate row to $+\Delta V$, which may correspond to −5 volts and +5 volts respectively Relaxing the pixel is accomplished by setting the appropriate column to $+V_{bias}$, and the appropriate row to the same $+\Delta V$, producing a zero volt potential difference across the pixel. In those rows where the row voltage is held at zero volts, the pixels are stable in whatever state they were originally in, regardless of whether the column is at $+V_{bias}$, or $-V_{bias}$. As is also illustrated in FIG. 4, it will be appreciated that voltages of opposite polarity than those described above can be used, e.g., actuating a pixel can involve setting the appropriate column to $+V_{bias}$, and the appropriate row to $-\Delta V$. In this embodiment, releasing the pixel is accomplished by setting the appropriate column to $-V_{bias}$, and the appropriate row to the same $-\Delta V$, producing a zero volt potential difference across the pixel.

FIG. 5B is a timing diagram showing a series of row and column signals applied to the 3×3 array of FIG. 2 which will result in the display arrangement illustrated in FIG. 5A, where actuated pixels are non-reflective. Prior to writing the frame illustrated in FIG. 5A, the pixels can be in any state, and in this example, all the rows are at 0 volts, and all the columns are at +5 volts. With these applied voltages, all pixels are stable in their existing actuated or relaxed states.

In the FIG. 5A frame, pixels (1,1), (1,2), (2,2), (3,2) and (3,3) are actuated. To accomplish this, during a "line time" for row 1, columns 1 and 2 are set to −5 volts, and column 3 is set to +5 volts. This does not change the state of any pixels, because all the pixels remain in the 3-7 volt stability window. Row 1 is then strobed with a pulse that goes from 0, up to 5 volts, and back to zero. This actuates the (1,1) and (1,2) pixels and relaxes the (1,3) pixel. No other pixels in the array are affected. To set row 2 as desired, column 2 is set to −5 volts, and columns 1 and 3 are set to +5 volts. The same strobe applied to row 2 will then actuate pixel (2,2) and relax pixels (2,1) and (2,3). Again, no other pixels of the array are affected. Row 3 is similarly set by setting columns 2 and 3 to −5 volts, and column 1 to +5 volts. The row 3 strobe sets the row 3 pixels as shown in FIG. 5A. After writing the frame, the row potentials are zero, and the column potentials can remain at either +5 or −5 volts, and the display is then stable in the arrangement of FIG. 5A. It will be appreciated that the same procedure can be employed for arrays of dozens or hundreds of rows and columns. It will also be appreciated that the timing, sequence, and levels of voltages used to perform row and column actuation can be varied widely within the general principles outlined above, and the above example is exemplary only, and any actuation voltage method can be used with the systems and methods described herein.

Figure 6A:
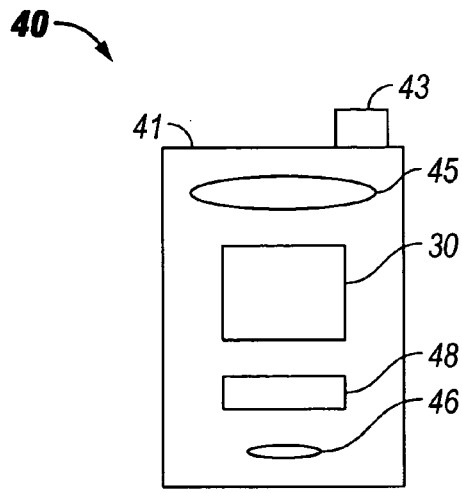
FIGS. 6A and 6B are system block diagrams illustrating an embodiment of a visual display device comprising a plurality of interferometric modulators.
Figure 6B:
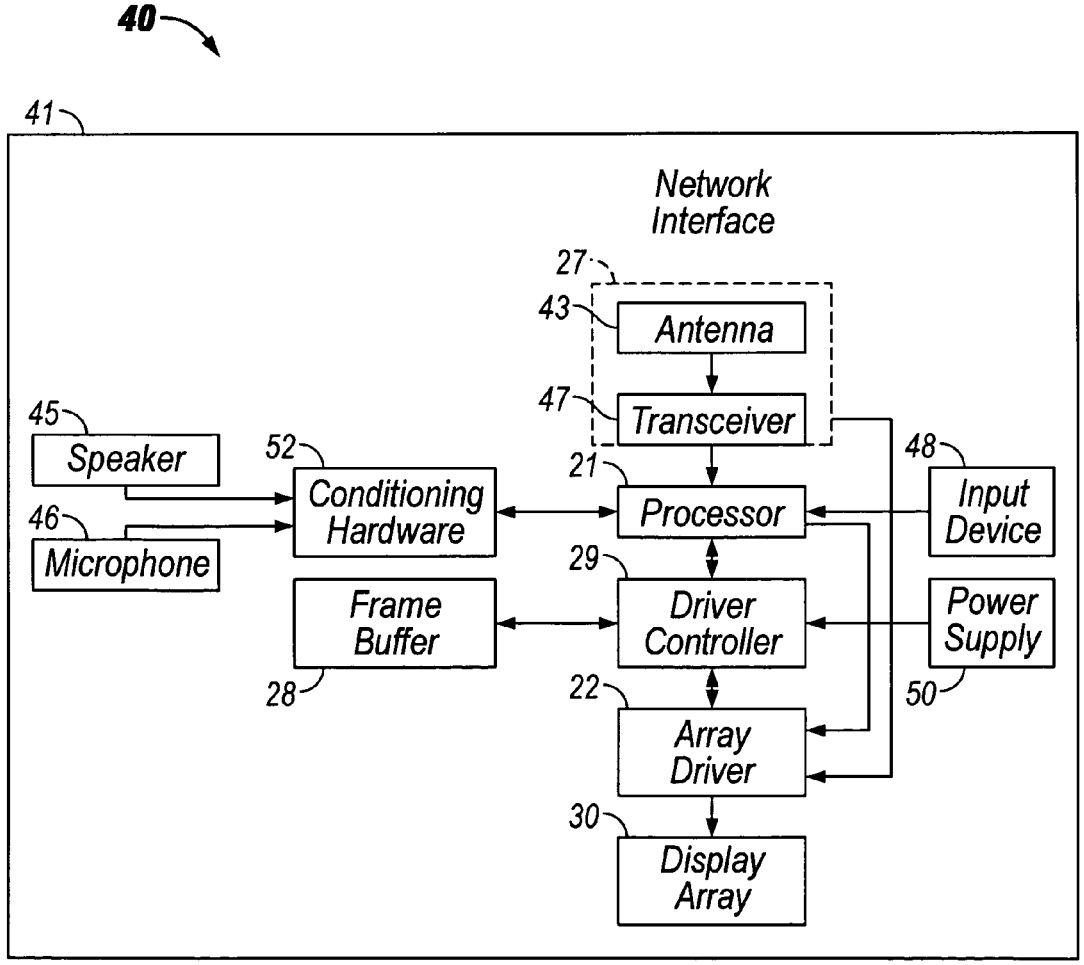

FIGS. 6A and 6B are system block diagrams illustrating an embodiment of a display device 40. The display device 40 can be, for example, a cellular or mobile telephone. However, the same components of display device 40 or slight variations thereof are also illustrative of various types of display devices such as televisions and portable media players.

The display device 40 includes a housing 41, a display 30, an antenna 43, a speaker 45, an input device 48, and a microphone 46. The housing 41 is generally formed from any of a variety of manufacturing processes as are well known to those of skill in the art, including injection molding, and vacuum forming. In addition, the housing 41 may be made from any of a variety of materials, including but not limited to plastic, metal, glass, rubber, and ceramic, or a combination thereof. In one embodiment the housing 41 includes removable portions (not shown) that may be interchanged with other removable portions of different color, or containing different logos, pictures, or symbols.

The display 30 of exemplary display device 40 may be any of a variety of displays, including a bi-stable display, as described herein. In other embodiments, the display 30 includes a flat-panel display, such as plasma, EL, OLED, STN LCD, or TFT LCD as described above, or a non-flat-panel display, such as a CRT or other tube device, as is well known to those of skill in the art. However, for purposes of describing the present embodiment, the display 30 includes an interferometric modulator display, as described herein.

The components of one embodiment of exemplary display device 40 are schematically illustrated in FIG. 6B. The illustrated exemplary display device 40 includes a housing 41 and can include additional components at least partially enclosed therein. For example, in one embodiment, the exemplary display device 40 includes a network interface 27 that includes an antenna 43 which is coupled to a transceiver 47. The transceiver 47 is connected to the processor 21, which is connected to conditioning hardware 52. The conditioning hardware 52 may be configured to condition a signal (e.g. filter a signal). The conditioning hardware 52 is connected to a speaker 45 and a microphone 46. The processor 21 is also connected to an input device 48 and a driver controller 29. The driver controller 29 is coupled to a frame buffer 28 and to the array driver 22, which in turn is coupled to a display array 30. A power supply 50 provides power to all components as required by the particular exemplary display device 40 design.

The network interface 27 includes the antenna 43 and the transceiver 47 so that the exemplary display device 40 can communicate with one or more devices over a network. In one embodiment the network interface 27 may also have some processing capabilities to relieve requirements of the processor 21. The antenna 43 is any antenna known to those of skill in the art for transmitting and receiving signals. In one embodiment, the antenna transmits and receives RF signals according to the IEEE 802.11 standard, including IEEE 802.11(a), (b), or (g). In another embodiment, the antenna transmits and receives RF signals according to the BLUETOOTH standard. In the case of a cellular telephone, the antenna is designed to receive CDMA, GSM, AMPS or other known signals that are used to communicate within a wireless cell phone network. The transceiver 47 pre-processes the signals received from the antenna 43 so that they may be received by and further manipulated by the processor 21. The transceiver 47 also processes signals received from the processor 21 so that they may be transmitted from the exemplary display device 40 via the antenna 43.

In an alternative embodiment, the transceiver 47 can be replaced by a receiver. In yet another alternative embodiment, network interface 27 can be replaced by an image source, which can store or generate image data to be sent to the processor 21. For example, the image source can be a digital video disc (DVD) or a hard-disc drive that contains image data, or a software module that generates image data.

Processor 21 generally controls the overall operation of the exemplary display device 40. The processor 21 receives data, such as compressed image data from the network interface 27 or an image source, and processes the data into raw image data or into a format that is readily processed into raw image data. The processor 21 then sends the processed data to the driver controller 29 or to frame buffer 28 for storage. Raw data typically refers to the information that identifies the image characteristics at each location within an image. For example, such image characteristics can include color, saturation, and gray-scale level.

In one embodiment, the processor 21 includes a microcontroller, CPU, or logic unit to control operation of the exemplary display device 40. Conditioning hardware 52 generally includes amplifiers and filters for transmitting signals to the speaker 45, and for receiving signals from the microphone 46. Conditioning hardware 52 may be discrete components within the exemplary display device 40, or may be incorporated within the processor 21 or other components.

The driver controller 29 takes the raw image data generated by the processor 21 either directly from the processor 21 or from the frame buffer 28 and reformats the raw image data appropriately for high speed transmission to the array driver 22. Specifically, the driver controller 29 reformats the raw image data into a data flow having a raster-like format, such that it has a time order suitable for scanning across the display array 30. Then the driver controller 29 sends the formatted information to the array driver 22. Although a driver controller 29, such as a LCD controller, is often associated with the system processor 21 as a stand-alone Integrated Circuit (IC), such controllers may be implemented in many ways. They may be embedded in the processor 21 as hardware, embedded in the processor 21 as software, or fully integrated in hardware with the array driver 22.

Typically, the array driver 22 receives the formatted information from the driver controller 29 and reformats the video data into a parallel set of waveforms that are applied many times per second to the hundreds and sometimes thousands of leads coming from the display's x-y matrix of pixels.

In one embodiment, the driver controller 29, array driver 22, and display array 30 are appropriate for any of the types of displays described herein. For example, in one embodiment, driver controller 29 is a conventional display controller or a bi-stable display controller (e.g., an interferometric modulator controller). In another embodiment, array driver 22 is a conventional driver or a bi-stable display driver (e.g., an interferometric modulator display). In one embodiment, a driver controller 29 is integrated with the array driver 22. Such an embodiment is common in highly integrated systems such as cellular phones, watches, and other small area displays. In yet another embodiment, display array 30 is a typical display array or a bi-stable display array (e.g., a display including an array of interferometric modulators).

The input device 48 allows a user to control the operation of the exemplary display device 40. In one embodiment, input device 48 includes a keypad, such as a QWERTY keyboard or a telephone keypad, a button, a switch, a touch-sensitive screen, a pressure- or heat-sensitive membrane. In one embodiment, the microphone 46 is an input device for the exemplary display device 40. When the microphone 46 is used to input data to the device, voice commands may be provided by a user for controlling operations of the exemplary display device 40.

Power supply 50 can include a variety of energy storage devices as are well known in the art. For example, in one embodiment, power supply 50 is a rechargeable battery, such as a nickel-cadmium battery or a lithium ion battery. In another embodiment, power supply 50 is a renewable energy source, a capacitor, or a solar cell, including a plastic solar cell, and solar-cell paint. In another embodiment, power supply 50 is configured to receive power from a wall outlet.

In some implementations control programmability resides, as described above, in a driver controller which can be located in several places in the electronic display system. In some cases control programmability resides in the array driver 22. Those of skill in the art will recognize that the above-described optimization may be implemented in any number of hardware and/or software components and in various configurations.

Figure 7A:
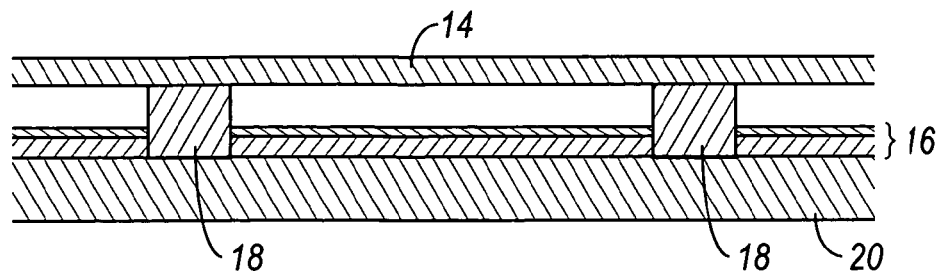
FIG. 7A is a cross section of the device of FIG. 1.
Figure 7B:
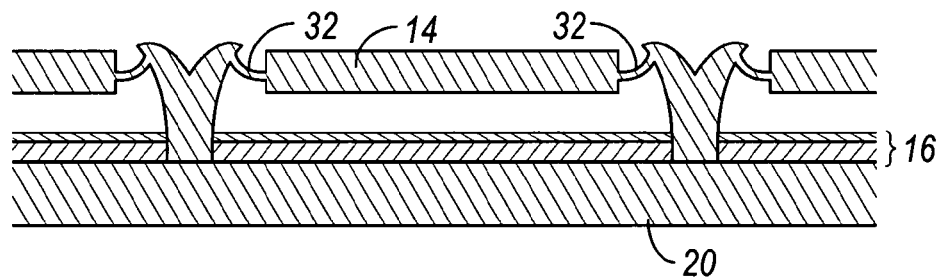
FIG. 7B is a cross section of an alternative embodiment of an interferometric modulator.
Figure 7C:
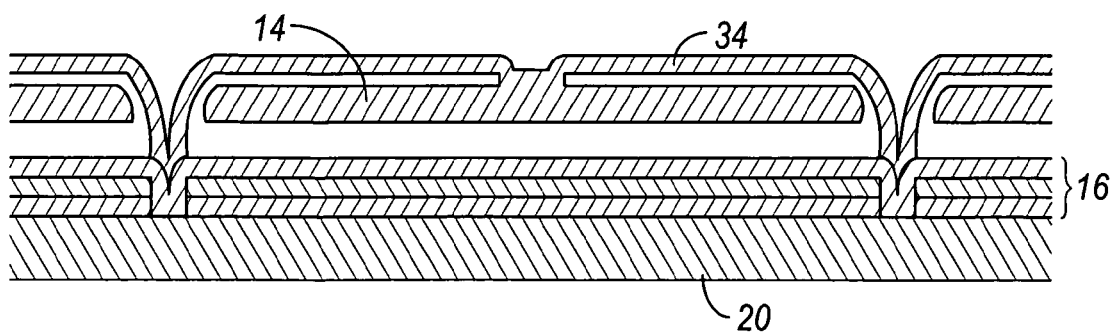
FIG. 7C is a cross section of another alternative embodiment of an interferometric modulator.
Figure 7D:
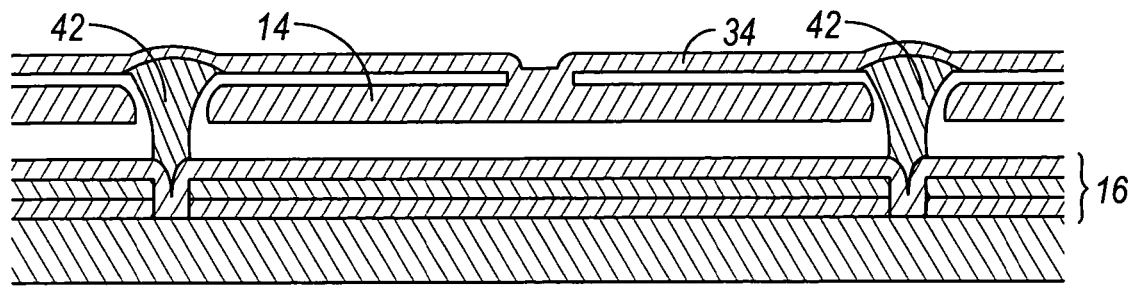
FIG. 7D is a cross section of yet another alternative embodiment of an interferometric modulator.
Figure 7E:
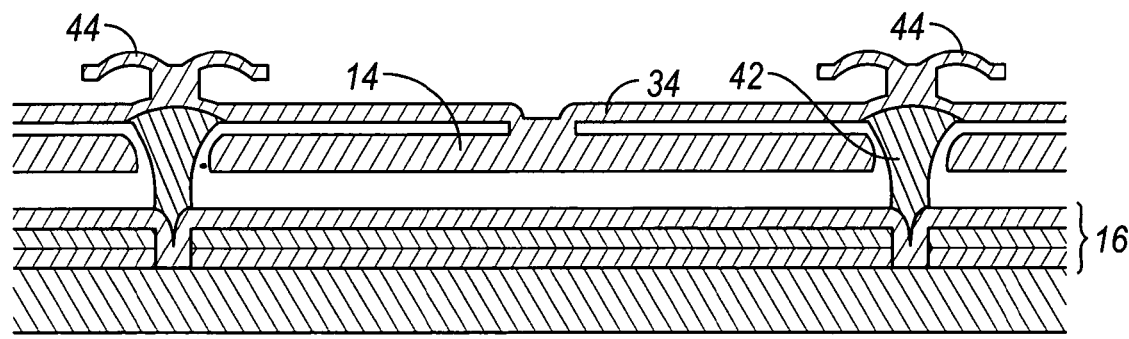
FIG. 7E is a cross section of an additional alternative embodiment of an interferometric modulator.

The details of the structure of interferometric modulators that operate in accordance with the principles set forth above may vary widely. For example, FIGS. 7A-7E illustrate five different embodiments of the movable reflective layer 14 and its supporting structures. FIG. 7A is a cross section of the embodiment of FIG. 1, where a strip of metal material 14 is deposited on orthogonally extending supports 18. In FIG. 7B, the moveable reflective layer 14 is attached to supports at the corners only, on tethers 32. In FIG. 7C, the moveable reflective layer 14 is suspended from a deformable layer 34, which may comprise a flexible metal. The deformable layer 34 connects, directly or indirectly, to the substrate 20 around the perimeter of the deformable layer 34. These connections are herein referred to as support posts. The embodiment illustrated in FIG. 7D has support post plugs 42 upon which the deformable layer 34 rests. The movable reflective layer 14 remains suspended over the cavity, as in FIGS. 7A-7C, but the deformable layer 34 does not form the support posts by filling holes between the deformable layer 34 and the optical stack 16. Rather, the support posts are formed of a planarization material, which is used to form support post plugs 42. The embodiment illustrated in FIG. 7E is based on the embodiment shown in FIG. 7D, but may also be adapted to work with any of the embodiments illustrated in FIGS. 7A-7C as well as additional embodiments not shown. In the embodiment shown in FIG. 7E, an extra layer of metal or other conductive material has been used to form a bus structure 44. This allows signal routing along the back of the interferometric modulators, eliminating a number of electrodes that may otherwise have had to be formed on the substrate 20.

In embodiments such as those shown in FIG. 7, the interferometric modulators function as direct-view devices, in which images are viewed from the front side of the transparent substrate 20, the side opposite to that upon which the modulator is arranged. In these embodiments, the reflective layer 14 optically shields some portions of the interferometric modulator on the side of the reflective layer opposite the substrate 20, including the deformable layer 34 and the bus structure 44. This allows the shielded areas to be configured and operated upon without negatively affecting the image quality. This separable modulator architecture allows the structural design and materials used for the electromechanical aspects and the optical aspects of the modulator to be selected and to function independently of each other. Moreover, the embodiments shown in FIGS. 7C-7E have additional benefits deriving from the decoupling of the optical properties of the reflective layer 14 from its mechanical properties, which are carried out by the deformable layer 34. This allows the structural design and materials used for the reflective layer 14 to be optimized with respect to the optical properties, and the structural design and materials used for the deformable layer 34 to be optimized with respect to desired mechanical properties.

Process Control Monitors

Many MEMS manufacturing processes consist of a series of material deposition and patterning steps. Various materials may be serially deposited on a substrate to form layers. Patterning with material etching between deposition steps may be used to structurally tailor the deposited material to achieve the desired MEMS structure. The multiple layer approach to MEMS manufacturing and the small scale of the structures created presents problems in trying evaluate whether the manufacturing process has produced structures and layers of materials having the desired properties. Accordingly, in one embodiment, process control monitors are provided that may be used to evaluate the results of various manufacturing processes. In some embodiments, the process control monitors are produced using at least some of the same manufacturing steps used to manufacture a MEMS device. Evaluation of these process control monitors may then be used to determine properties of various materials and structures formed during those manufacturing steps. In some embodiments, the process control monitors are produced using the same set of material deposition and patterning steps used during the manufacturing. The process control monitors may be structurally tailored by applying different patterns to the process control monitor than is applied to the MEMS structure. For example, one layer of material present in the MEMS structure may be completely absent in the process control monitor by patterning the process control monitor in such a way that the entire layer deposited is etched away during an etching step. Similarly, in other embodiments, a layer of material normally etched away during manufacture of the MEMS structure may remain in the process control monitor.

In some embodiments, information from the process control monitor may be obtained through optical means. For example, light reflected from the process control monitor may contain information regarding the materials present in the process control monitor. Those of skill in the art will appreciate other methods of evaluating process control monitors such as laser scanning, microscopy including optical, electron, and x-ray microscopy, and spectroscopy. In one embodiment, the light reflected is detected with a photodetector to obtain the intensity of reflected light. This information may be used to determine the reflectance and transmittance of materials in the process control monitor. These properties may in turn provide information regarding the thicknesses of materials in the process control monitor. For example, the amount of reflectance from an inherently reflective material will provide a measure of its thickness. In one embodiment, a Minolta® reflectometer is used. In another embodiment, the light reflected from the process control monitor is measured with a spectrometer to obtain the wavelength dependence of the reflected light. This wavelength dependence can provide information regarding the absorptive properties of the materials in the process control monitor and the index of refraction of the materials. Furthermore, because MEMS devices often contain reflective surfaces in close proximity, reflected light may undergo constructive and destructive interference (e.g., the MEMS device may contain one or more etalon). Therefore, the wavelength dependence of the reflected light can provide information regarding the relative positioning of reflective surfaces in the MEMS. In one embodiment, a measured spectrum is fit to a model spectrum predicted to be reflected from an etalon in order to determine properties such as the depth of the etalon. In some embodiments, a colorimeter is used to measure the color of light reflected from the process control monitor. As used herein, an "etalon" refers to two surfaces that are at least partially reflective positioned such that light may enter through one surface and be reflected between the two surfaces multiple times before reflecting back through the same surface. The multiple reflectances can lead to destructive and constructive interference at various wavelengths, allowing for the filtering of optical wavelengths.

In one embodiment, a transparent substrate may be used to support the process control monitor. Such a substrate enables optical detection from the side opposite the deposition side. Thus, in some cases, lower deposited materials may be probed where they could not otherwise be (e.g., where the upper layers include a highly reflective layer). In other embodiments, a process control monitor is optically probed from the side of material deposition.

Figure 8:
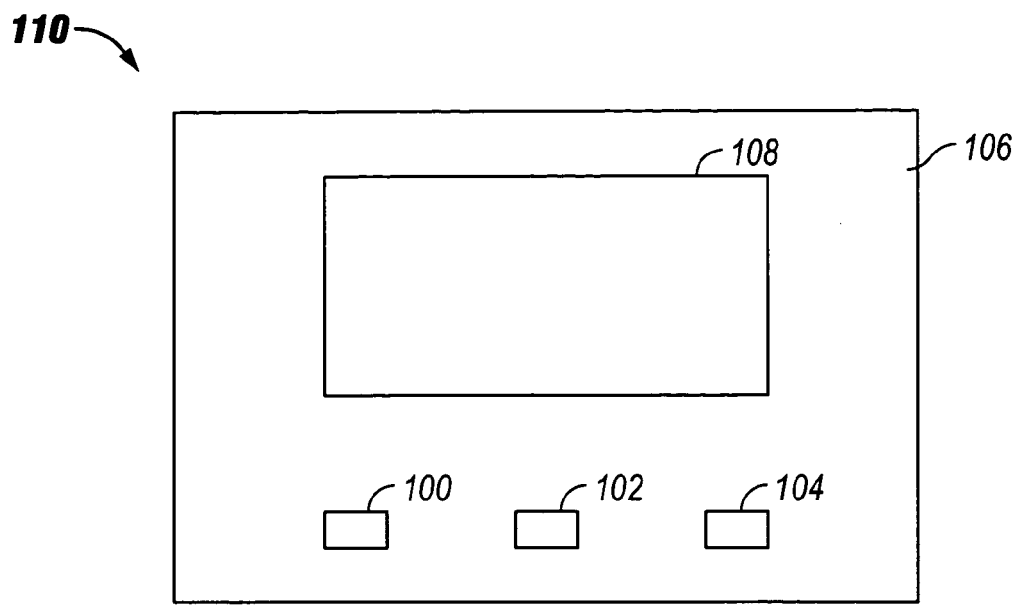
FIG. 8 is a top view of a wafer comprising a MEMS structure and multiple process control monitors.

In one embodiment, with reference to FIG. 8, process control monitors 100, 102, and 104 may be formed on the same substrate 106 at the same time as the MEMS device 108 is being formed. As discussed above, all of the substrate 106 may be exposed to the same material deposition and patterning steps, however, different patterns may be applied to form the process control monitors 100, 102, and 104. For example, the pattern applied to the process control monitors 100, 102, and 104 during a patterning step may be different then the pattern applied to the MEMS device 108 during a corresponding patterning step. The patterning steps may include any suitable patterning technique in the art (e.g. photolithography). Any number of different process control monitors 100, 102, and 104 may be formed on the substrate. The integrated wafer 110 depicted in FIG. 8 allows the probing of the processes applied during the manufacturing of the specific MEMS device 108. Thus, any anomalous results can be quickly identified before the MEMS device 108 is tested electrically or incorporated into a packaged device, thereby avoiding additional expense. In some embodiments, the process control monitors 100, 102, and 104 may also be probed after manufacture of the MEMS device 108. In one embodiment, the MEMS device 108 consists of an array of interferometric modulators suitable for use in a display. In some embodiments, the process control monitors on the substrate 106 are labeled during manufacturing.

Etalon Based Process Control Monitors

As noted above, in some embodiments, process control monitors are constructed such that they contain at least one etalon. The spectrum of light reflected from the etalon may then be detected and fit to an etalon model to determine properties of the process control monitor, and hence properties of analogous structures in the MEMS device. In some embodiments, the process control monitors are formed by the same material deposition steps as the MEMS device and thus contain at least some of the material layers found in the MEMS device. In some embodiments, the number of layers found in the process control monitors is less than the number found in the MEMS device.

Figure 9:
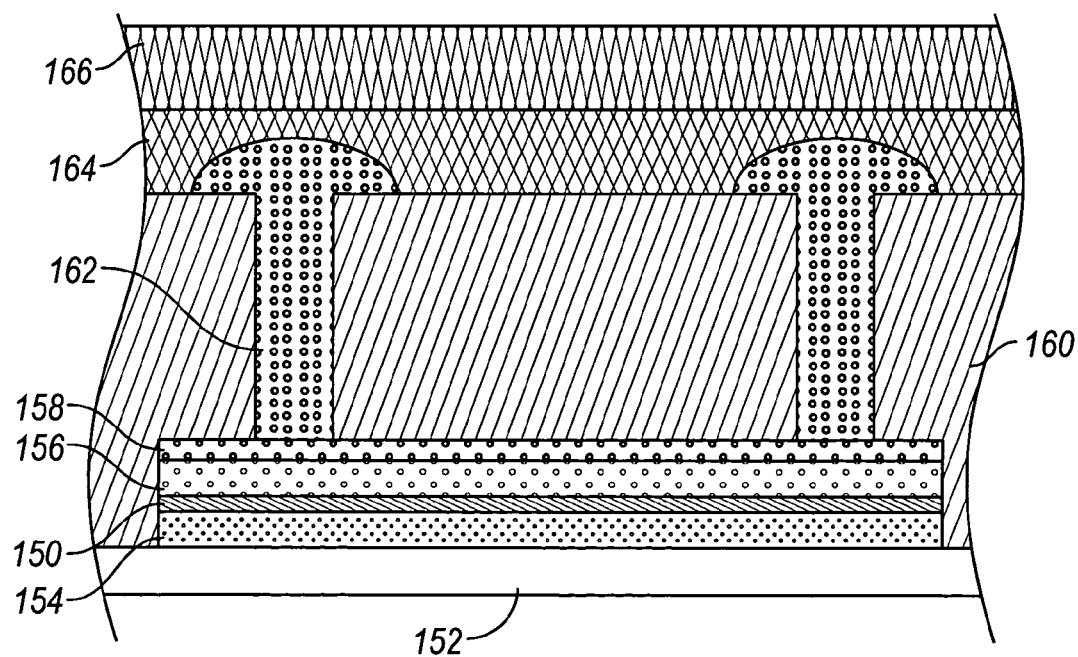
FIG. 9 is a cross section of layers deposited during manufacture of an interferometric modulator.

One set of examples of etalon based process control monitors are structures that contain less than all of the layers found an in interferometric modulator but nonetheless still contain an etalon. FIG. 9 depicts an example of materials that may be deposited during manufacture of an interferometric modulator. First, a layer of indium-tin-oxide (ITO) 154 is deposited onto a transparent substrate 152. The ITO 154, which is a transparent conductor, provides a conductive plate so that a voltage can be applied between the movable mirror in the interferometric modulator and the plate. In one embodiment, the ITO is about 500 Å thick. Next, a layer of chrome 150 is deposited. In one embodiment, the chrome 150 is relatively thin (in one embodiment, approximately 70 Å), allowing it to act as a partial reflector. Alternatively, the chrome layer 150 may be deposited onto the substrate 152 followed by the ITO layer 154. Next, a dielectric layer 156/158 is deposited. The dielectric layer may consist of one or more oxides. In some embodiments, the oxide layer 156/158 may be a composite layer. For example, a relatively thick layer of $SiO_2$ 156 (in one embodiment, approximately 450 Å) may be deposited followed by a thin layer of $Al_2O_3$ 158 (in one embodiment, approximately 70 Å) to protect the $SiO_2$ 156. In some embodiments, three or more oxide layers may be used (e.g., $Al_2O_3$—$SiO_2$—$Al_2O_3$). The oxide layer 156/158 provides an insulating layer between the movable mirror and the chrome 150. The thickness of the layer determines the interference properties of the interferometric modulator, particularly when it is in an actuated state. In the next step, a sacrificial layer 160 is deposited (in one embodiment, approximately 2000 Å). The sacrificial layer provides a space filling material that can be easily etched away without affecting the other materials. In one embodiment, the sacrificial layer 160 is molybdenum. Other examples of suitable materials for the sacrificial layer include polysilicon, amorphous silicon, or photoresist. In the last step of manufacturing, the sacrificial layer 160 will be etched away to create an air gap between the movable mirror and the oxide layer 156,158. Patterning and etching of the sacrificial layer 160 may be used to create holes and trenches in the layer for the formation of posts and rails that will support the movable mirror. Planar material 162 may be applied to fill the holes and form the posts. Finally, the mechanical membrane 164/166 containing the movable mirror is formed. In one embodiment, the mechanical membrane 164/166 is formed by an aluminum layer 164 (in one embodiment, approximately 500 Å) followed by a nickel layer (in one embodiment, approximately 1450 Å) 166. In some embodiments, an additional aluminum layer is added on top of the nickel layer to provide better adhesion of photoresist used during patterning. After etching away the sacrificial layer 160 in the structure depicted in FIG. 9, an interferometric modulator similar to that depicted in FIG. 7A is obtained. In some embodiments, a dark mask layer may be added to the transparent substrate 152 prior to addition of the other layers. The dark mask layer may be patterned to reduce reflection from portions of the structure such as posts or rails. In some embodiments, the dark mask layer includes a MoCr layer and an oxide layer. Those of skill in the art will appreciate that patterning and etching steps in addition to those mentioned here may be used to form an interferometric modulator. Furthermore, it will be appreciated that other structures of interferometric modulators are possible, as for example depicted in FIGS. 7B-7E.

Figure 10A:
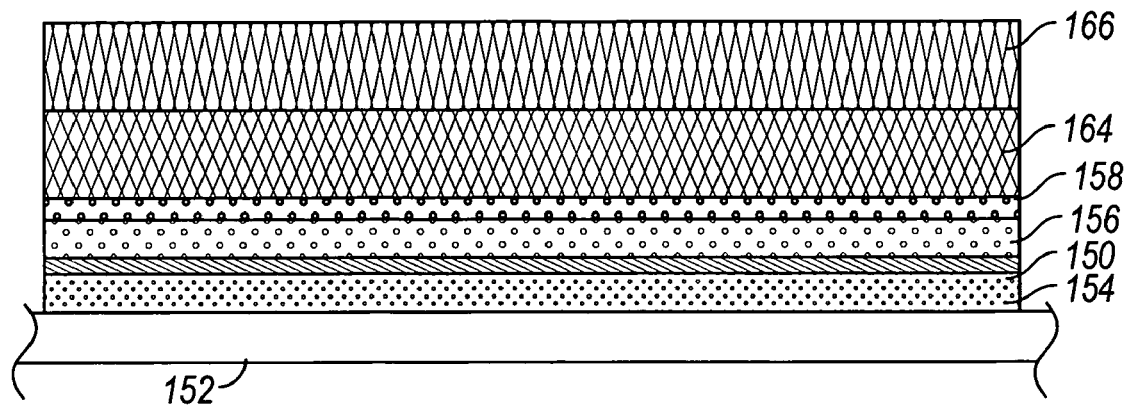
FIG. 10A is a cross section of layers in an etalon-based process control monitor for use in monitoring a process used to manufacture the interferometric modulator of FIG. 9.

Examples of etalon based process control monitors containing some of the material layers discussed above are depicted in FIGS. 10A-10D. The process control monitor depicted in FIG. 10A contains the ITO 154, chrome 150, oxide 156/158, and mechanical membrane 164/166 layers deposited on top of each other onto the substrate 152. The partially reflective chrome layer 150 and the reflective mechanical membrane 164/166 form an etalon whose reflectance may be measured from the bottom side of the substrate 152. Analyzing the spectrum of light reflected from this etalon or its color can provide an indication of the combined thickness of the oxide 156/158 layers and their index of refractions and the thickness and reflectivity of the chrome 150 layer. It will also be appreciated that this configuration approximates that obtained when an interferometric modulator is in an actuated state (i.e., the mirror is collapsed against the oxide layer). Therefore, evaluating these process control monitors will provide an indication of whether interferometric modulators produced by the process used will have the desired actuated spectral characteristics.

Figure 10B:
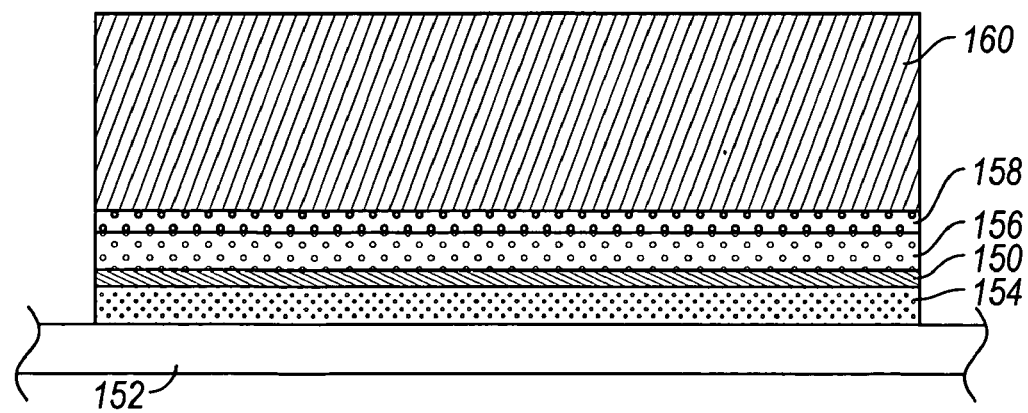
FIG. 10B is a cross section of layers in another etalon-based process control monitor for use in monitoring a process used to manufacture the interferometric modulator of FIG. 9.

The process control monitor depicted in FIG. 10B consists of the ITO 154, chrome 150, oxide 156/158, and sacrificial layer 160. As mentioned above, the sacrificial layer 160 may be molybdenum, which is inherently reflective. Accordingly, an etalon is formed by the partially reflective chrome layer 150 and the reflective sacrificial layer 160. In addition to providing the same parameters regarding the oxide 156/158 layers and the actuated interferometric modulator state as discussed above, reflectance from this process control monitor may provide information regarding the sacrificial layer 160. For example, reflectance from the sacrificial layer 160 will depend on the thickness of the sacrificial layer 160. In some embodiments, the sacrificial layer 160 is removed by etching and the remaining ITO 154, chrome 150, and oxide 156/158 layers analyzed to determined if the sacrificial layer 160 has interacted with any of the remaining layers.

Figure 10C:
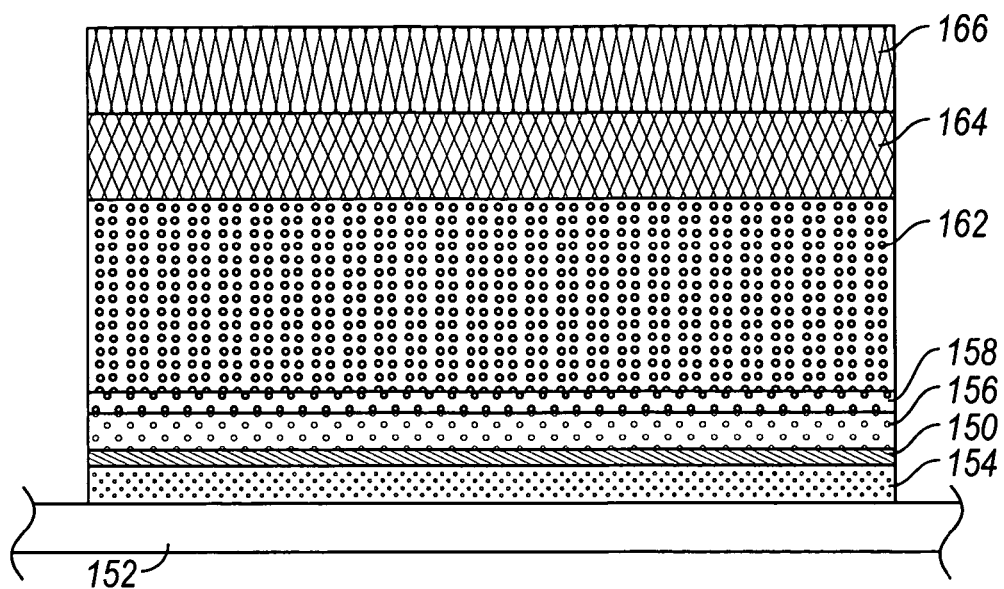
FIG. 10C is a cross section of layers in another etalon-based process control monitor for use in monitoring a process used to manufacture the interferometric modulator of FIG. 9.

The process control monitor depicted in FIG. 10C contains the ITO 154, chrome 150, oxide 156/158, planar 162, and mechanical membrane 164/166 layers. An etalon is formed by the chrome 150 and mechanical membrane 164/166 layers. Analyzing the spectrum of reflected light and comparing it to the results obtained for the process control monitor in FIG. 10A can provide the index of refraction of the planar material and its thickness. Furthermore, the optical response from this process control monitor will approximate that caused by the areas of an interferometric modulator array where there are posts or rails.

Figure 10D:
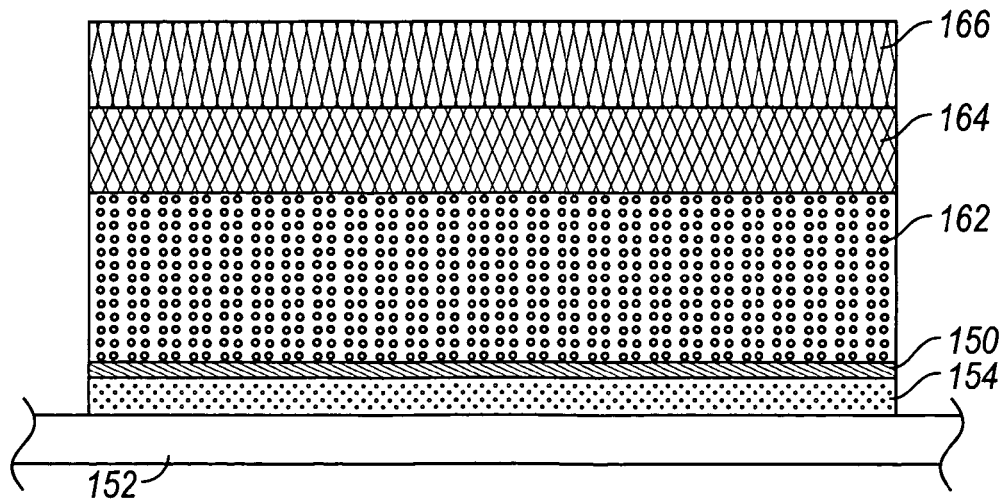
FIG. 10D is a cross section of layers in another etalon-based process control monitor for use in monitoring a process used to manufacture the interferometric modulator of FIG. 9.

The process control monitor depicted in FIG. 10D contains the ITO 154, chrome 150, planar 162, and mechanical membrane 164/166 layers. An etalon is formed by the chrome 150 and mechanical membrane 164/166 layers. Analyzing the spectrum of reflected light can provide the index of refraction of the planar material 162 as well as the thickness of the planar 162 material. Comparison with the process control monitor of FIG. 10D can provide information regarding the oxide layers 156/158 (e.g., indices of refraction and thickness).

When the etalon based process control monitors described above are formed by the same deposition and patterning steps as used to manufacture interferometric modulators, as for example when it is formed on the same substrate 106 as an interferometric modulator array 108 (see FIG. 8), then appropriate patterning may be applied so that layers that are not desired in the process control monitor are etched away. For example, in the process control monitor depicted in FIG. 10A, the sacrificial layer 160 and planar 162 material deposited during manufacturing may be etched away. In some embodiments, it may be desirable to protect regions of the process control monitors to prevent etching away of layers during processing. For example, deposited planar material or material from the mechanical membrane 164/166 may be patterned so that it remains on the edges of the process control monitor to protect the sacrificial layer 160 during the release etch if it is desirable to have a process control monitor containing the sacrificial layer 160.

Those of skill in the art will appreciate many other combinations of layers deposited in a process control monitor whose optical properties (e.g., interference properties) may provide information about the corresponding material formed during manufacturing of a MEMS device.

Non-Etalon Based Process Control Monitors

In some embodiments, process control monitors are constructed that do not contain two reflective surfaces forming an etalon. In these process control monitors, information regarding the materials in the monitors can be obtained through reflectance and/or transmittance measurements. These reflectance and/or transmittance values may be correlated to film thicknesses. In some embodiments, the process control monitors are formed by the same material deposition steps as the MEMS device and thus contain at least some of the material layers found in the MEMS device. In some embodiments, the number of layers found in the process control monitors is less than the number found in the MEMS device. The reflectance and/or transmittance characteristics of these structures may help identify any errors that occurred during processing of the elements included in the process control monitor structures. These process control monitor structures may be evaluated using any suitable detector such as a reflectometer, photodetector, spectrometer, or calorimeter. In one embodiment, the reflectance of the film is measured using a spherical integrator and reflectometer. These process control monitor structures enable the processing of individual elements in the MEMS structures to be monitored to determine any errors and to optimize the manufacturing process.

FIGS. 11A-11G depict one set of examples of non-etalon based process control monitors that contain less than all layers of material deposited during manufacture of interferometric modulators such as depicted in FIG. 9. The process control monitor in FIG. 11A consists of the ITO layer 154 and the chrome layer 150 deposited onto the substrate 152. The reflectivity of this process control monitor provides an indication of the thickness of the chrome layer 150 and the transparency of the ITO layer 154. In order for the chrome layer 150 to act as a partially reflective mirror in an interferometric modulator, the film making up the partial reflector may be very thin. For example, the film may have a thickness of about 70 Å. The thickness of such thin films are difficult to measure and verify. Therefore, in one embodiment, the thickness of the chrome layer 150 is determined by measuring the reflectance of the layer in the process control monitor of FIG. 11A. As the thickness of the film increases, so will the reflectance. Therefore, by calibrating film thickness with measured reflectance for a given material, the thickness can be easily determined from a measured reflectance. The optical properties of the process control monitor of FIG. 11A also approximate the optical properties observed in an interferometric modulator array between columns where the mechanical membrane and oxide layers have been removed. Accordingly, these process control monitors can be used to determine if the intercolumn properties are acceptable for using the array as a display.

In another embodiment, a process control monitor containing only the chrome layer 150 on the substrate 152 may be used to determine the reflectance, and hence the thickness, of the chrome layer 150. Measurements of this process control monitor may be compared to those obtained for the process control monitor depicted in FIG. 11A to determine the optical properties of the ITO layer 154. For example, reflectance from the surface of the ITO layer 154 may be proportional to the ratio of the reflectance from the two process control monitors. In some embodiments, a chrome-only process control monitor may manufactured on a wafer separate from that used to manufacture the interferometric modulators if the processing conditions for the interferometric modulators cannot be used to create a chrome-only layer.

Figure 11A:
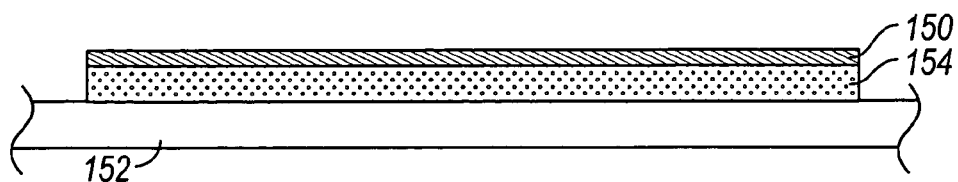
FIG. 11A is a cross section of layers in a non-etalon-based process control monitor for use in monitoring a process used to manufacture the interferometric modulator of FIG. 9.
Figure 11B:
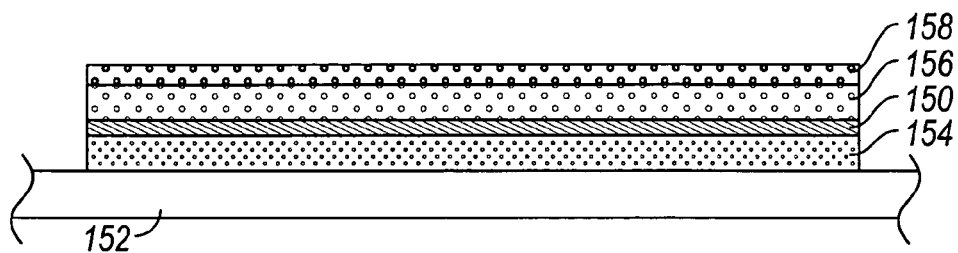
FIG. 11B is a cross section of layers in another non-etalon-based process control monitor for use in monitoring a process used to manufacture the interferometric modulator of FIG. 9.

FIG. 11B depicts another embodiment of a non-etalon based process control monitor structure that consists of the ITO layer 154, chrome layer 150, and oxide layer 156/158. This structure may be used to measure the optical characteristics of the ITO-chrome-oxide combination. For example, measuring the transmittance through the process control monitor provides an indication of the combined attenuation caused by the ITO layer 154, chrome layer 150, and oxide layer 156/158. Comparison of the measurements of this process control monitor structure with the measurements of the process control monitor in FIG. 11A can be used to isolate the optical properties of the oxide layer 156/158. In addition to providing information regarding the optical characteristics of the oxide layer 156/158, the comparison can also be used to determine the thickness of the oxide layer 156/158 (e.g., a lower transmittance will indicate a thicker oxide layer 156/158). The optical properties of the process control monitor in FIG. 11B also approximates those observed in an interferometric modulator array in the area of the etch release holes in the mechanical membrane.

Figure 11C:
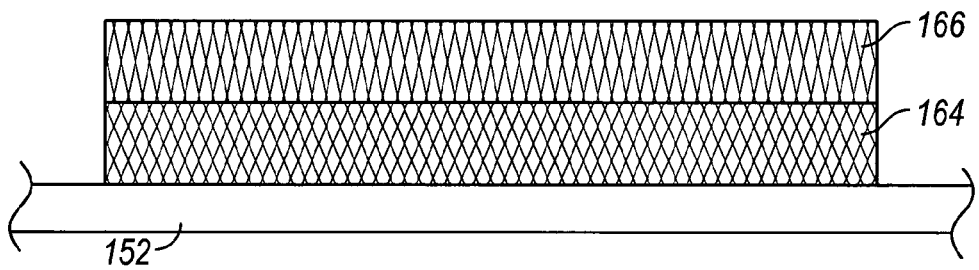
FIG. 11C is a cross section of layers in another non-etalon-based process control monitor for use in monitoring a process used to manufacture the interferometric modulator of FIG. 9.

FIG. 11C depicts another embodiment of a process control monitor structure that consists of the mechanical membrane layer 164/166. This process control monitor may be used to isolate and measure the reflective properties of the mechanical membrane layer 164/166.

Figure 11D:
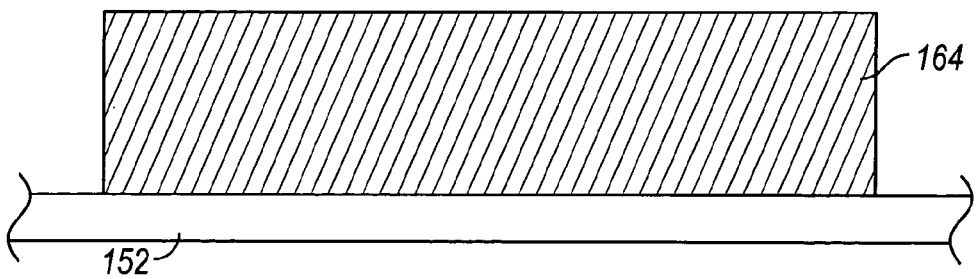
FIG. 11D is a cross section of layers in another non-etalon-based process control monitor for use in monitoring a process used to manufacture the interferometric modulator of FIG. 9.

FIG. 11D depicts still another embodiment of a process control monitor structure consisting only of the sacrificial layer 160 deposited onto the substrate 152. This process control monitor may be used to measure characteristics of the sacrificial layer 160 alone, including its thickness. This process control monitor may be analyzed prior to any release etch. Alternatively a layer of a protective material may be deposited over the sacrificial layer 160 to protect it during a release etch.

Figure 11E:
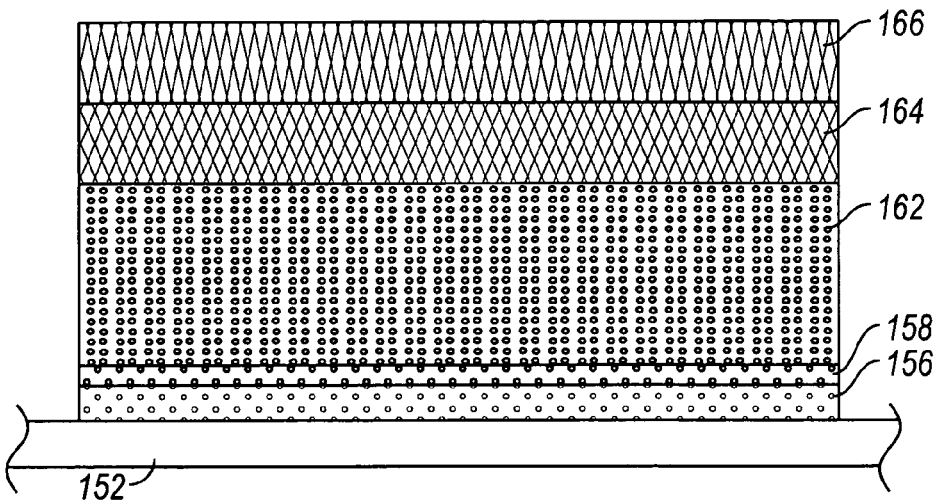
FIG. 11E is a cross section of layers in another non-etalon-based process control monitor for use in monitoring a process used to manufacture the interferometric modulator of FIG. 9.

FIG. 11E depicts another embodiment of a process control monitor having oxide layers 156/158, planar material 162, and mechanical membrane layer 164/166. The reflectance from this process control monitor approximates that observed in an interferometric modulator array between rows where cuts in the ITO 154 and chrome 158 layers have been made.

Figure 11F:
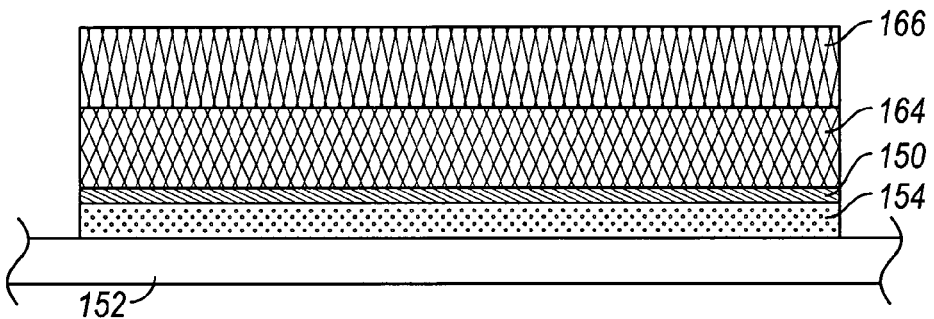
FIG. 11F is a cross section of layers in another non-etalon-based process control monitor for use in monitoring a process used to manufacture the interferometric modulator of FIG. 9.

FIG. 11F depicts an embodiment of a process control monitor having the ITO layer 154, chrome layer 150, and mechanical membrane layer 164/166. Because the chrome layer 150 and mechanical membrane layer 164/166 will together act is a reflector, the reflectance from this process control monitor can provide information regarding the transparency, thickness, and index of refraction of the ITO layer 154. Furthermore, the reflectance from this process control monitor may be compared with that for FIG. 11A to isolate the optical properties of the chrome layer 150. In other words, the results from testing this process monitor may be used to subtract the optical effects of the ITO layer 154 in the process control monitor of FIG. 11A.

Figure 11G:
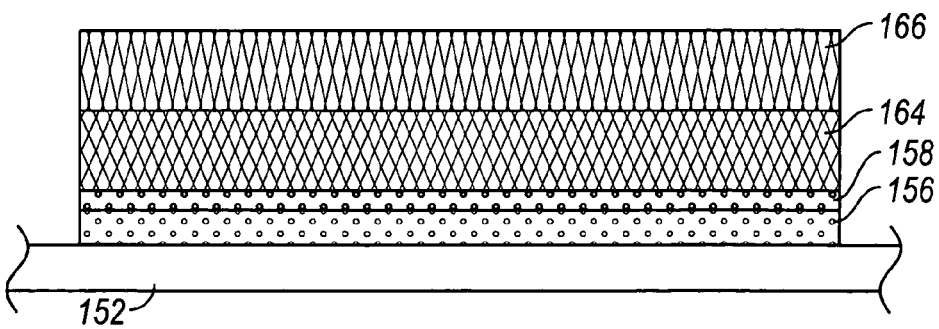
FIG. 11G is a cross section of layers in another non-etalon-based process control monitor for use in monitoring a process used to manufacture the interferometric modulator of FIG. 9.

FIG. 11G depicts still another embodiment of a process control monitor that comprises the oxide layer 156/158 and the mechanical membrane layer 164/166. Because the mechanical membrane layer 164/166 acts as a strong reflector, this process control monitor may be used to determine the transparency, thickness, and index of refraction of the oxide layer 156/158.

As for the etalon based process control monitors, the non-etalon based process control monitors described above may be formed by the same deposition and patterning steps as used to manufacture the interferometric modulators. Appropriate patterning may be applied so that layers that are not desired in the process control monitor are etched away. In addition, appropriate protection against etching may be applied.

Those of skill in the art will appreciate many other combinations of layers deposited in a process control monitor whose optical properties (e.g., reflectance and/or transmittance) may provide information about the corresponding material formed during manufacturing of a MEMS device.

Release Etch Process Control Monitors

Figure 12:
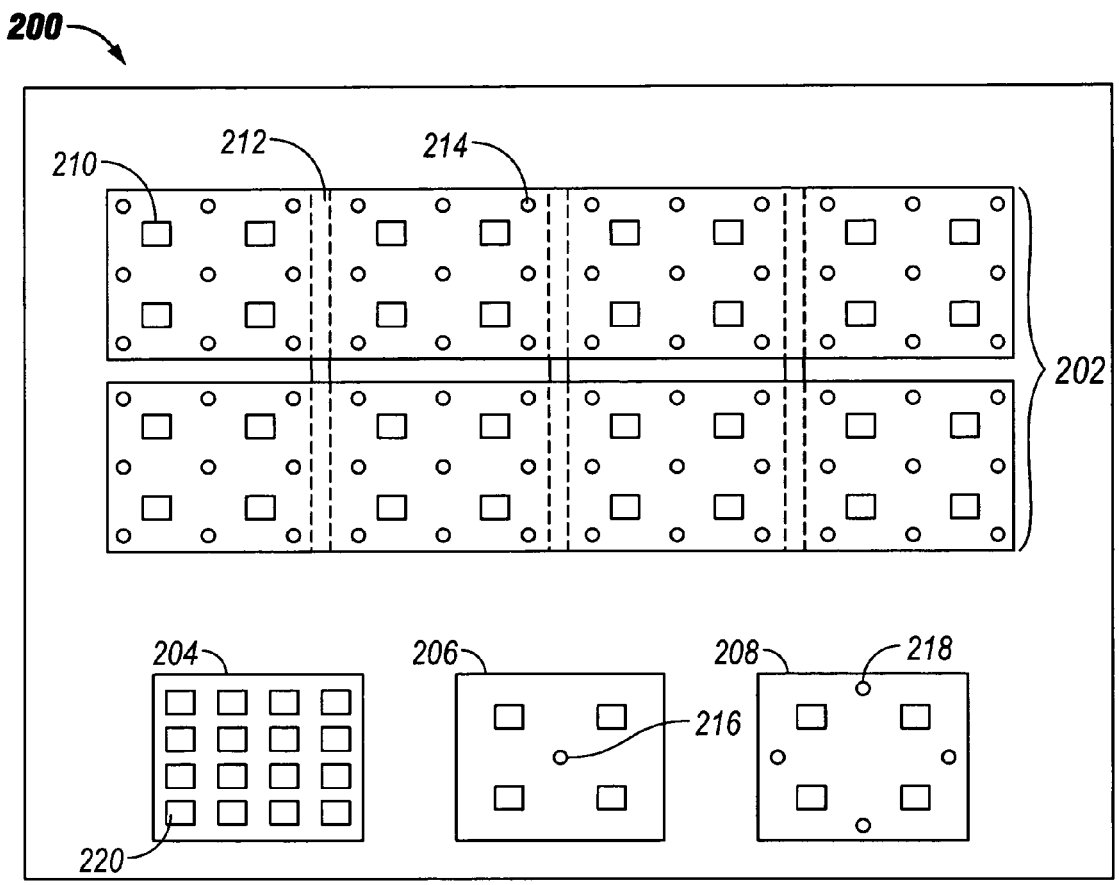
FIG. 12 is a top view of a wafer comprising an interferometric modulator array and process control monitors used to monitor release etching and color reflected from the interferometric modulators.

The rate and extent of the release etch process during MEMS manufacture may be monitored using a release etch or spatial process control monitor. FIG. 12 depicts a wafer 200 containing an interferometric modulator array 202 and a series of process control monitors 204, 206, and 208. The interferometric modulator array 202 contains a number of posts 210 and rails 212 to support the mechanical membrane. A series of etch holes 214 are formed into the mechanical membrane so that etchant can reach the sacrificial layer during the release etch. For the manufacturing to be successful, the sacrificial layer should be completely removed from the array region. Accordingly, in one embodiment, process control monitors are provided to monitor the rate and extent of release etching.

One such process control monitor is depicted in process control monitor 206. This process control monitor 206 consists of the same interferometric modulator structure as present in the array 202, however, only a single hole 216 is patterned into the mechanical membrane. The distance between the hole 216 and the edges of the process control monitor 206 is greater than the distance between the holes 214 in the interferometric modulator array 202. Because the process control monitor 206 contains only a single hole 216 as opposed to multiple holes 214, not all of the sacrificial layer can be removed from the process control monitor 206 in the amount of time it takes the release etchant to remove the entire sacrificial layer in the array 202. As the etching in the process control monitor 206 proceeds, the area of the process control monitor where the sacrificial layer has been removed will contrast in color from the areas where the etchant has not yet reached as observed from the side of the substrate opposite the process side. In cases where a reflective sacrificial layer is used (e.g., molybdenum), this contrast is due to the different etalons formed. Where the sacrificial layer is still present, an etalon will be formed between the chrome layer and the reflective sacrificial layer. Where the sacrificial layer has been removed, an etalon will be formed between the chrome layer and the reflective mechanical membrane. Thus, the color observed where the sacrificial layer has been removed will approximate the color of an unactuated interferometric modulator (e.g., a bright state) while the color observed where the sacrificial layer remains will approximate the color of an actuated interferometric modulator (e.g., a dark state). The distance from the center of the hole 216 to the boundary of color change (e.g., the radius) will provide a measure of the extent of etching. This process control monitor may be used to measure the rate and extent of etching either during the process itself (i.e., in-situ) or after its completion.

A similar etch-release process control monitor is depicted by the process control monitor 208. In this process control monitor, multiple holes 218 are formed in the mechanical membrane, however, the distance between each hole 218 is greater than the distance between the holes 214 in the interferometric modulator array 202. Thus, etching in the process control monitor 208 will be incomplete after the entire sacrificial layer has been removed from the interferometric modulator array 202. A distance indicating the extent of etching may be measured from the center of each hole 218 in the process control monitor 208.

Figure 13A:
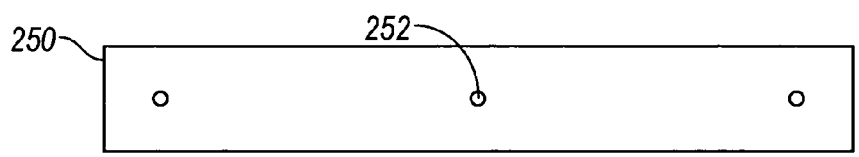
FIG. 13A is a top view of a process control monitor that can be used to monitor release etching.
Figure 13B:
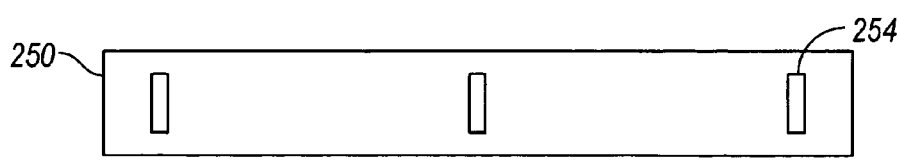
FIG. 13B is a top view of another process control monitor that can be used to monitor release etching.

Etch-release process control monitors as described above may take on any suitable shape. For example, instead of a structure similar to that found in the interferometric modulator array, the process control monitor may consist of a strip shape 250 with one or more holes 252 in the mechanical membrane, as depicted in FIG. 13A. The extent of etching may then be measured by determining the linear distance from the holes 252 along the strip 250 to where etching has extended. In another embodiment, depicted in FIG. 13B, holes having the shape of rectangular slots 254 are formed into the strip 250 instead of holes having a circular shape. In some embodiments, a plurality of slots 254 are provided having varying widths (e.g., 3 μm, 4 μm, 5 μm).

In some embodiments, planarization or other protective material may be patterned around the edges of the process control monitor to provide a seal to protect against the release etchant from reaching the sacrificial layer from the edges. Accordingly, the sacrificial layer will only be removed by etchant entering the etch release holes. In some embodiments, the mechanical membrane in the etch release process control monitor may be electrically shorted to the ITO/chrome layers.

The extent of etching may be measured using the process control monitors described above by visually observing the process control monitors or by electronically imaging the process control monitors, such as by using a CCD camera, and then computationally analyzing the image so that the measuring is automated. In some embodiments, posts in the process control monitor may be used as a vernier for determining the extant of etching. For example, posts may be formed in the process control monitor having a known distance from each other. The number of posts along a line from the center of the hole may then be used to approximate the distance. In some embodiments, a higher density of posts than formed in the interferometric modulators may be used to provide a more precise measurement. Those of skill in the art will appreciate many other shapes and structures that may be used to measure the extent of etching.

Interferometric Modulator Process Control Monitors

In one embodiment, the interference properties (e.g., the spectrum of reflected light) of interferometric modulators may be determined by using a process control monitor that consists of an interferometric modulator with enhanced stability. Such process control monitors may be constructed so that the mechanical membrane is resistant to movement, and therefore fixed in position, forming a static etalon. In one embodiment, such process control monitors may be formed by using a substantially transparent dielectric layer (e.g., an oxide layer) in place of the sacrificial layer. The reflective mechanical membrane will thus rest against the dielectric layer and be in a fixed position. Such a process control monitor may advantageously be manufactured separately from a display interferometric modulator array so that a thicker oxide layer can be deposited than is deposited during typical interferometric modulator manufacture.

In another embodiment, a process control monitor is formed that may be manufactured by the same material depositions as a display interferometric modulator array. For example, as depicted in FIG. 12, a process control monitor 204 may be constructed that comprises a higher density of posts 220 than is found in the interferometric modulator array 202. The higher density of posts 220 provide increased positional stability to the mechanical membrane that they support. Accordingly, even under application of an electric potential (e.g., less than about 10 volts, 15 volts, or 20 volts), the mechanical membrane in the process control monitor 204 will resist moving toward the ITO layer and thereby, reflect the same spectrum of light. As used herein, by "posts" it is meant any intermittent structure that may be used to support a mechanical membrane. Accordingly, it is intended that "posts" include "point" structures consisting essentially of a vertical linear structure. It is also intended that "posts" include structures consisting essentially of a strip of vertical material, also known as rails.

Process control monitors having stable mechanical membranes, such as described above, may be used to optimize manufacturing to produce interferometric modulators that will reflect a desired spectrum of light. Furthermore, such process control monitors provide a quick check of the success of a manufacturing process. In some embodiments, where a manufacturing process produces an array of interferometric modulators that reflect different colors (e.g., for use in a polychromatic display), multiple process control monitors as described above may be used, each reflecting the corresponding color. Alternatively, a single process control monitor may be formed having different regions where each region has posts having a different height than other regions. Thus, each region will reflect a different color light.

Thickness Process Control Monitors

Still another type of process control monitor is used to measure the thickness of each layer deposited during processing. In one embodiment, thickness process control monitors are manufactured such that a single step is formed from the substrate to the top of the process control monitor. The step height of the single step will thus correspond to the combined thickness of the all the layers of the process control monitor at the location of the step. Non-limiting examples of layers that may be deposited include the ITO and chrome layers, the oxide layers, the sacrificial layer, planarization on the sacrificial layer, mechanical membrane layer on the oxide layers, and mechanical membrane layers on the sacrifical layer on the oxide layers.

Figure 14:
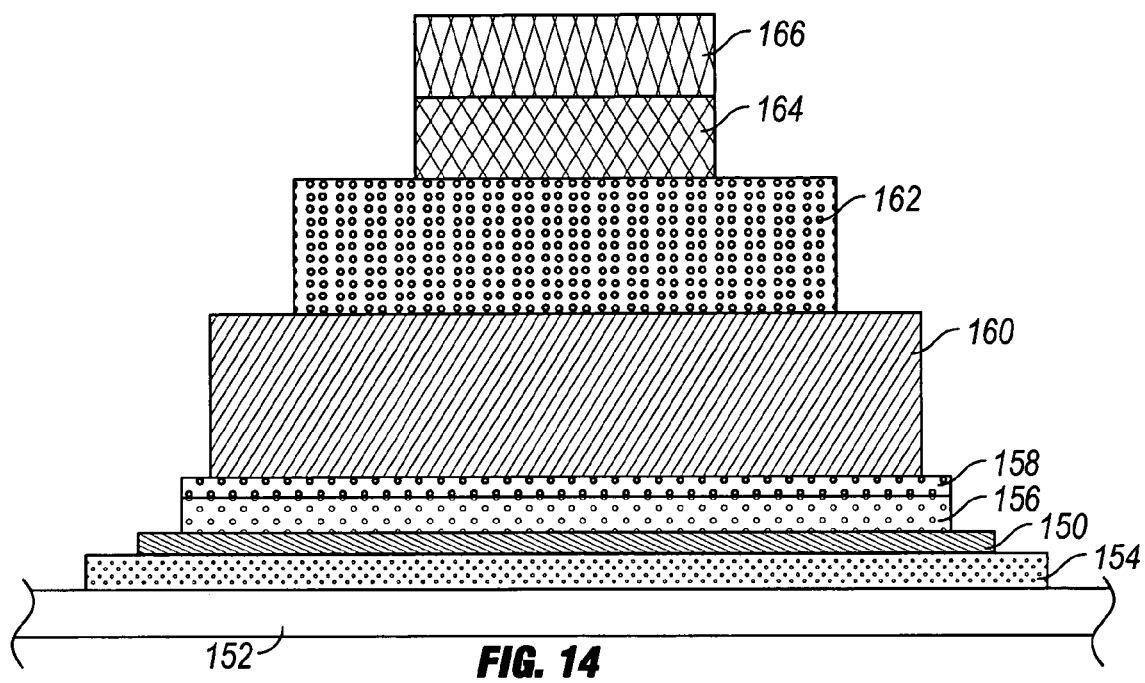
FIG. 14 is a cross section of a process control monitor that can be used to measure the thickness of layers in interferometric modulators.

In another embodiment, multiple layer process control monitors are formed such that a stack with a stair-step pattern profile may be formed. The step heights will correspond to the thickness of one or more deposited layers. For example, the resulting process control monitor may have a structure similar to that in FIG. 14. The process control monitor in FIG. 14 contains each of the layers deposited during manufacturing of an interferometric modulator, such as the one depicted in FIG. 9. The process control monitor provides steps corresponding to the thickness of the ITO layer 154, the chrome layer 150, the oxide layers 156/158, the sacrificial layer 160, the planar material 162, and the mechanical membrane, 164/166. The thickness of each step may be measured in a single sweep of an appropriate thickness measuring technique rather than having to measure each layer in a separate process control monitor. In a non-limiting example, a stylus-based surface profiler (e.g., a profilometer), such as available from KLA-Tencor may be used to measure step heights by a single sweep of the stylus and thus quickly determine the thickness of each layer deposited in a particular interferometric modulator manufacturing run. The stair step pattern reduces the natural bounce encountered when using profilometers and thereby improves accuracy as compared to sweeping across each layer individually. Those of skill in the art will recognize that any combination of layers may be used in a multi-stair step pattern. Thus, not all layers deposited during manufacture of interferometric modulators need to be included.

Figure 15:
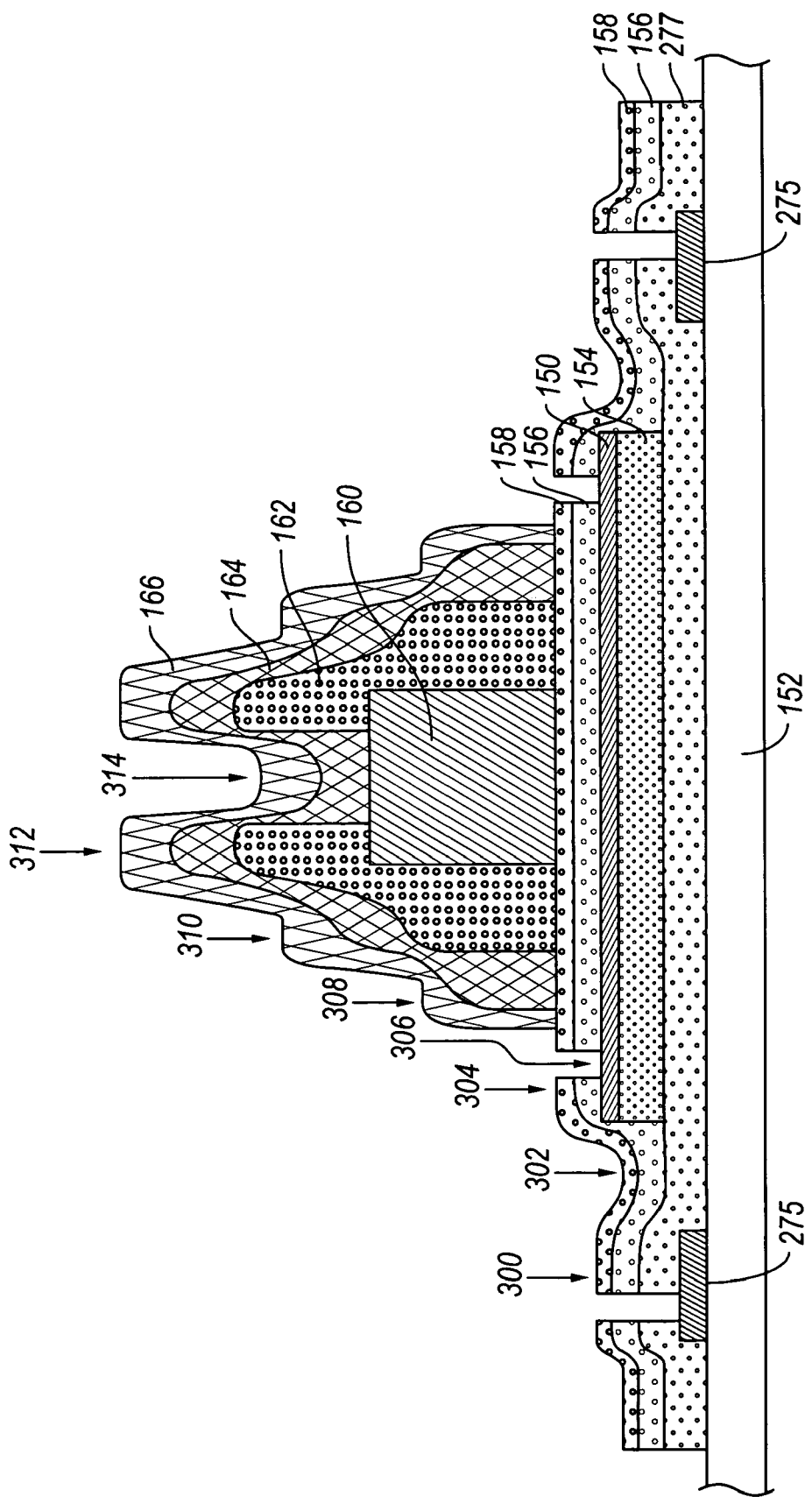
FIG. 15 is a cross section of another embodiment of a process control monitor that can be used to measure the thickness of layers in the process control monitor.

Another embodiment of a thickness process control monitor is depicted in FIG. 15. This process control monitor also has a stair-step profile; however, the stair-step pattern formed does not monotonically increase in height. One advantage of such a pattern is that the step heights may be formed to more closely correspond to actual thicknesses present in some interferometric modulators. In addition to layers discussed above, the process control monitor of FIG. 15 also contains a dark mask layer 275. The dark mask layer 275 may be used in interferometric modulators to inhibit reflection from some static structures such as posts and rails. In this embodiment, an additional oxide layer 277 may be deposited above the dark mask layer 275.

Step 300 in FIG. 15 corresponds to the combined thicknesses of all of the oxide layers (277, 156, and 158) and the dark mask 275. This step may be compared with step 302 to determine the thickness of the dark mask 275. The absolute height of step 304 provides the combined thickness of the oxide layers 277, 156, and 158 and the ITO 154 and chrome 150 layers. Comparison with step 302 provides the thickness of the combined ITO 154 and chrome 150 layers. Step 306 provides the thickness of the oxide layers 156/158 that are deposited on top of the ITO 154 and chrome 150 layers. Step 308 corresponds to the thickness of the mechanical membrane 164/166. The absolute height of step 308 will also approximate the combined thicknesses of material when an interferometric modulator is in an actuated state with the mechanical membrane 164/166 collapsed on top of the oxide layer 158. Step 310 corresponds to the combined thicknesses of the mechanical membrane 164/166 and the planar material 162. Comparison with step 308 may be used to determine the thickness of the planar material 162. Step 312 corresponds to the thickness of the sacrificial layer 160. Finally, step 314 corresponds to the thickness of the planar material 312. The absolute height of step 314 also corresponds to the position of the mechanical membrane 164/166 when an interferometric modulator is in an unactuated state.

Figure 16:
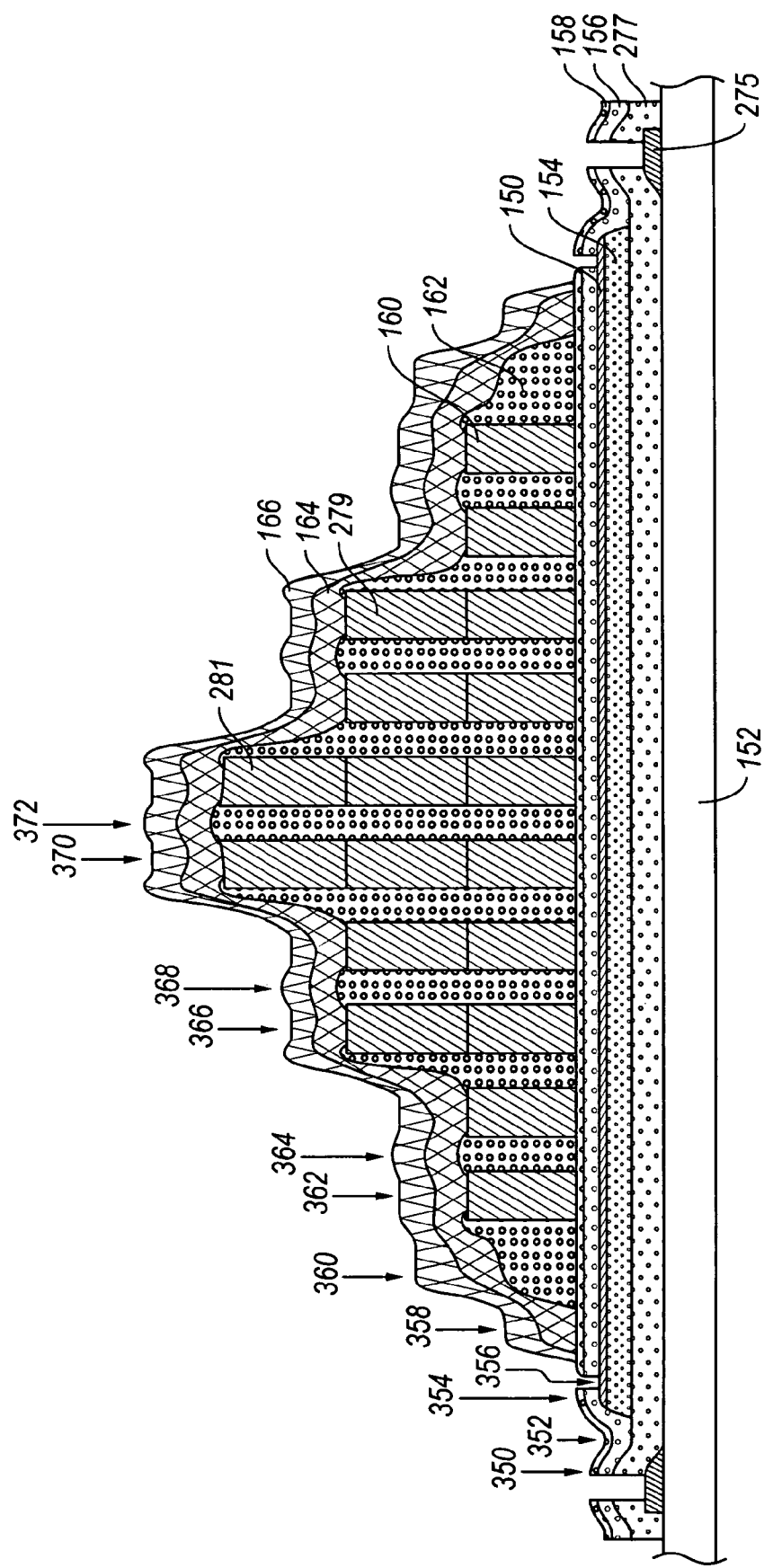
FIG. 16 is a cross section of yet another embodiment of a process control monitor that can be used to measure the thickness of layers in the process control monitor.

In some embodiments, polychromatic interferometric modulator displays are formed. One such polychromatic display uses interferometric modulators having different gap depths to reflect different colors. For example, interferometric modulators having three different gap depths adapted to reflect predominantly red, green, or blue colors may be employed. One method of forming such a polychromatic display is to deposit and pattern three sacrificial layers prior to deposition of the planar material and mechanical membrane layers. The patterning of the sacrificial layers may be such that a single layer remains for one set of interferometric modulators, two layers remain for another set of interferometric modulators, and three layers remain for a final set of interferometric modulators. After deposition of the mechanical membrane and release etching, a smaller gap depth will be formed where the single sacrificial layer was formed, a medium gap depth will be formed where two sacrificial layers were formed, and a larger gap depth will be formed where three sacrificial layers were formed. FIG. 16 depicts a thickness process control monitor that may be used to measure layer thicknesses formed during use of such a three-sacrificial layer process. In addition to sacrificial layer 160, sacrificial layers 279 and 281 are also formed. Those of skill in the art will appreciate that the sacrificial layers 160, 279, and 281 may be deposited sequentially or they may be deposited in a different order if liftoff or etch back techniques are utilized. Step 350 corresponds to the combined thicknesses of all of the oxide layers (277, 156, and 158) and the dark mask 275. This step may be compared with step 352 to determine the thickness of the dark mask 275. The absolute height of step 354 provides the combined thickness of the oxide layers 277, 156, and 158 and the ITO 154 and chrome 150 layers. Comparison with step 352 provides the thickness of the combined ITO 154 and chrome 150 layers. The comparison of step 356 with step 354 provides the thickness of the oxide layers 156/158 that are deposited on top of the ITO 154 and chrome 150 layers. Step 358 corresponds to the thickness of the mechanical membrane 164/166. The absolute height of step 358 also approximates the combined thicknesses of material when an interferometric modulator is in an actuated state with the mechanical membrane 164/166 collapsed on top of the oxide layer 158. Step 360 corresponds to the combined thicknesses of the mechanical membrane 164/166 and the planar material 162. Comparison with step 358 may be used to determine the thickness of the planar material 162.

Step 362 corresponds to the combined thickness of the mechanical membrane 164/166 and the single sacrificial layer 160. Comparison of step 362 with step 358 provides the thickness of the sacrificial layer 160. The absolute height of step 362 also corresponds to the position of the mechanical membrane 164/166 when the interferometric modulator having the smallest gap depth is in an unactuated state. The absolute height of step 364 corresponds to the combined height in an interferometric modulator array over a post that is between two interferometric modulators having the smallest gap depth. Comparison of step 364 with step 358 provides the height of the post. In a similar manner, step 366 corresponds to the combined thickness of the mechanical membrane 164/166 and the first 160 and second 279 sacrificial layers. Comparison of step 366 with step 362 provides the thickness of the second sacrificial layer 279. The absolute height of step 366 also corresponds to the position of the mechanical membrane 164/166 when the interferometric modulator having the medium gap depth is in an unactuated state. The absolute height of step 368 corresponds to the combined height in an interferometric modulator array over a post that is between two interferometric modulators having the medium gap depth. Comparison of step 368 with step 358 provides the height of the post. Step 370 corresponds to the combined thickness of the mechanical membrane 164/ 166 and first 160, second 279, and third 281 sacrificial layers. Comparison of step 370 with step 366 provides the thickness of the third sacrificial layer 281. The absolute height of step 370 also corresponds to the position of the mechanical membrane 164/166 when the interferometric modulator having the largest gap depth is in an unactuated state. The absolute height of step 372 corresponds to the combined height in an interferometric modulator array over a post that is between two interferometric modulators having the largest gap depth. Comparison of step 372 with step 358 provides the height of the post.

The process control monitor of FIG. 16 provides for the accurate measurement of the gap depths produced by a particular interferometric modulator manufacturing process. Measuring the cumulative height of the sacrificial layers corresponding to the medium and large gap depth interferometric modulators provides a more accurate indication of the resulting gap depth than would be obtained by measuring the individual thicknesses of the three sacrificial layers. If the three layers were measured separately, local variation in the thickness of each layer would be compounded when the thicknesses are added together to obtain total gap depths. In contrast, the process control monitor of FIG. 16 provides single measurements of the combined thicknesses the sacrificial layers, reducing errors introduced by local variances in each separate sacrificial layer.

In the embodiments of FIGS. 15 and 16, the mechanical membrane 164/166 may be used to protect the sacrificial layer 160 in the process control monitors during the release etch. Accordingly, in some embodiments, the thickness process control monitors may be evaluated after release etch. In some other embodiments, thickness process control monitors may be evaluated prior to the release etch. If the results indicate a problem with one or more layer thicknesses, the wafer may be scrapped prior to the release etch, thereby saving time and money.

Those of skill in the art will recognize that many other stair-step patterned process control monitors may be produced. It will also be appreciated that thickness process control monitors that contain less than all of the layers in a MEMS device may be constructed.

Although the invention has been described with reference to embodiments and examples, it should be understood that numerous and various modifications can be made without departing from the spirit of the invention. Accordingly, the invention is limited only by the following claims.

What is claimed is:

1. A process control monitor for monitoring the effect of a process for manufacturing interferometric modulators on the color of light reflected by those interferometric modulators, comprising a test etalon that comprises a higher density of posts supporting a mechanical membrane in the test etalon than in interferometric modulators produced by the process.

2. The process control monitor of claim 1, wherein the mechanical membrane in the test etalon has substantially the same structure as a mechanical membrane in the interferometric modulators produced by the process.

3. The process control monitor of claim 1, wherein, except for the higher density of posts, the process control monitor has substantially the same structure as the interferometric modulators produced by the process.

4. A method of monitoring the effect of a process for manufacturing interferometric modulators on the color of light reflected by those interferometric modulators, the method comprising:

forming a test etalon that comprises a higher density of posts supporting a mechanical membrane in the test etalon than in interferometric modulators produced by the process; and detecting light reflected from the test etalon.

5. The method of claim 4, wherein the test etalon comprises at least two regions, wherein the posts in one region have a different height than posts in the other region such that light reflected from the two regions are of different color.

6. The method of claim 4, wherein at least two test etalons are formed where the posts in one test etalon have a different height than posts in the other test etalon such that light reflected from the two test etalons are of different color.

7. The method of claim 4, wherein the reflected light is detected during forming of the test etalon.

8. The method of claim 4, wherein the reflected light is detected after forming of the test etalon.

9. The method of claim 4, wherein detecting the reflected light comprises measuring a color of the reflected light with a colorimeter.

10. The method of claim 4, wherein detecting the reflected light comprises measuring a spectrum of the reflected light with a spectrometer.

11. The method of claim 10, further comprising determining the depth of the test etalon from the detected light.

12. The method of claim 11, wherein the determining comprises fitting the measured spectrum to a model of etalon interference.

* * * * *

UNITED STATES PATENT AND TRADEMARK OFFICE
CERTIFICATE OF CORRECTION

PATENT NO.        : 7,369,252 B2
APPLICATION NO.   : 11/281758
DATED             : May 6, 2008
INVENTOR(S)       : Cummings et al.

It is certified that error appears in the above-identified patent and that said Letters Patent is hereby corrected as shown below:

Title Page, Item (56) Page 3, Col. 2, Line 44 (U.S. Patent Documents) please delete "Pichi et al." and insert -- Piehl et al. --, therefor.

Title Page, Item (56) Page 4, Col. 1, Line 6 (Other Publications) please delete "Actuatros," and insert -- Actuators, --, therefor.

Title Page, Item (56) Page 4, Col. 2, Line 1 (Other Publications) please delete ""Inteferometric" and insert -- "Interferometric --, therefor.

Title Page, Item (56) Page 4, Col. 2, Line 11 (Other Publications) please delete "Fabry-Perol" and insert -- Fabry-Perot --, therefor.

Title Page, Item (56) Page 4, Col. 2, Line 19 (Other Publications) please delete "sencorsmag" and insert -- sensorsmag --, therefor.

Title Page, Item (56) Page 5, Col. 2, Line 1 (Other Publications) please delete "Vaccuum" and insert -- Vacuum -- therefor.

Col. 19, Line 44, please delete "calorimeter" and insert -- colorimeter --, therefor.

Col. 23, Line 65, please delete "sacrifical" and insert -- sacrificial --, therefor.

Signed and Sealed this

Sixteenth Day of December, 2008

JON W. DUDAS
*Director of the United States Patent and Trademark Office*